(12) United States Patent
Daglow

(10) Patent No.: US 9,333,015 B2
(45) Date of Patent: May 10, 2016

(54) APPARATUS AND DEVICE FOR THE FIXATION OF OSTEOSYNTHESIS PLATES

(71) Applicant: Terry Daglow, Bonham, TX (US)

(72) Inventor: Terry Daglow, Bonham, TX (US)

(*) Notice: Subject to any disclaimer, the term of this patent is extended or adjusted under 35 U.S.C. 154(b) by 217 days.

(21) Appl. No.: 14/142,735

(22) Filed: Dec. 27, 2013

(65) Prior Publication Data
US 2014/0188181 A1 Jul. 3, 2014

Related U.S. Application Data

(60) Provisional application No. 61/746,403, filed on Dec. 27, 2012.

(51) Int. Cl.
A61B 17/58 (2006.01)
A61B 17/60 (2006.01)
A61F 2/00 (2006.01)
A61B 17/80 (2006.01)

(52) U.S. Cl.
CPC .................................. A61B 17/808 (2013.01)

(58) Field of Classification Search
None
See application file for complete search history.

(56) References Cited

U.S. PATENT DOCUMENTS 5,647,525 A * 7/1997 Ishizawa .................. B25C 1/00
227/113

* cited by examiner

Primary Examiner — Sameh Boles
(74) Attorney, Agent, or Firm — George M. Tompkins; Tompkins, P.C.

(57) ABSTRACT

Disclosed herein are apparatus, devices and methods for affixing an implant, plate, or the like to body tissue. Preferred embodiments comprise a plate with a pre-defined hole, fasteners configured for secure attachment to body tissue, and a self-centering tool capable of holding and installing multiple fasteners.

7 Claims, 24 Drawing Sheets

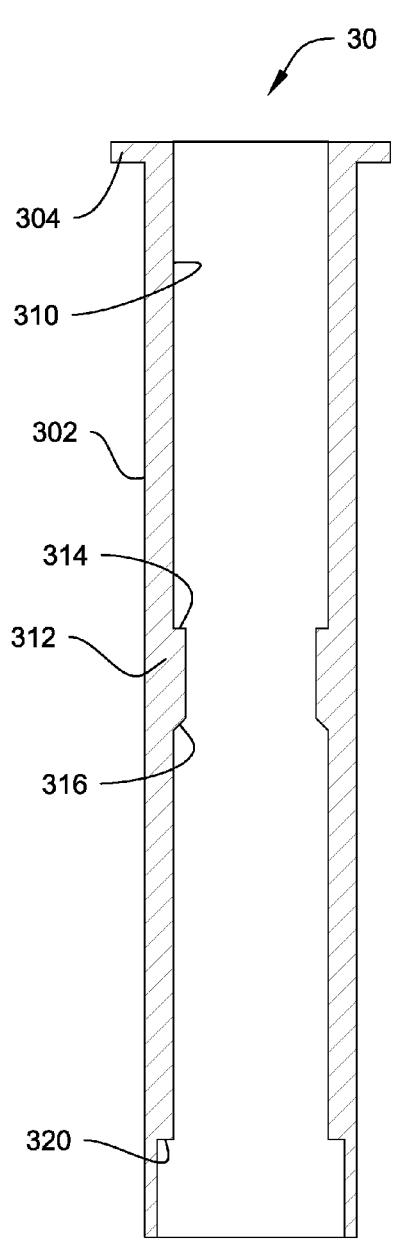
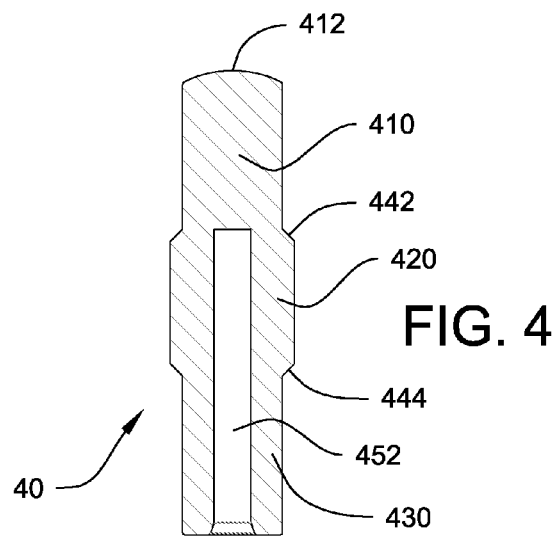
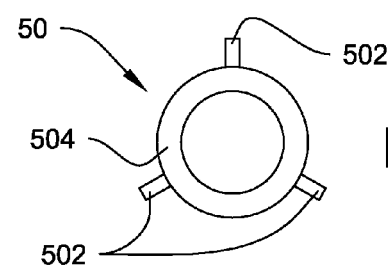
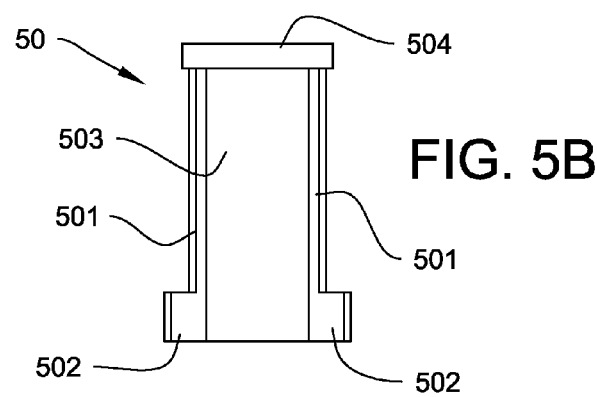
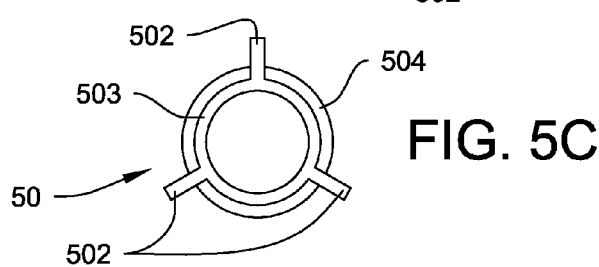
FIG. 3
FIG. 4
FIG. 5A
FIG. 5B
FIG. 5C

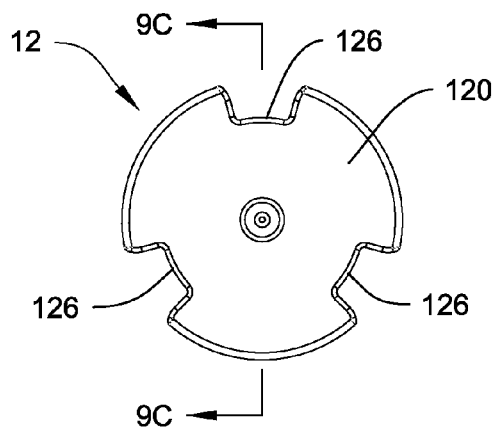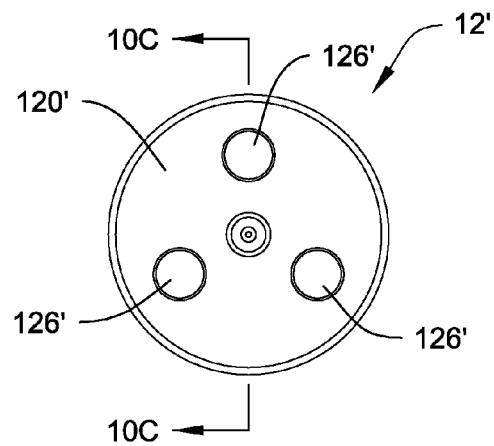
FIG. 9A  FIG. 10A
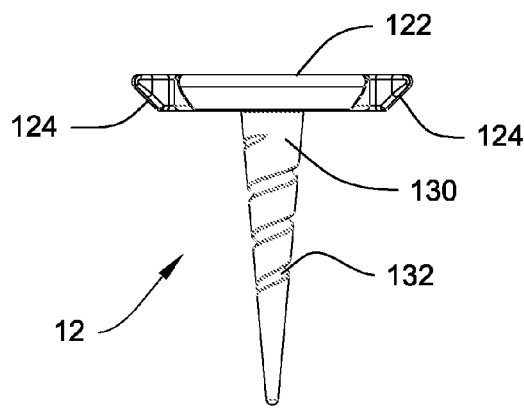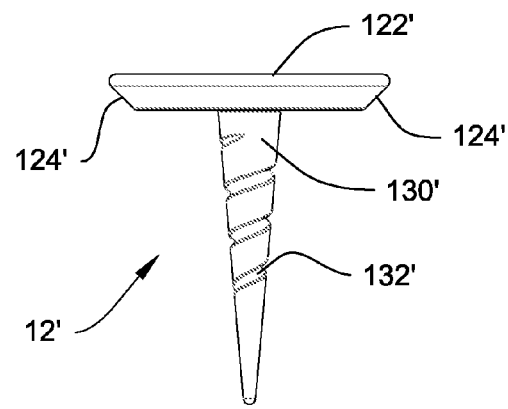
FIG. 9B  FIG. 10B
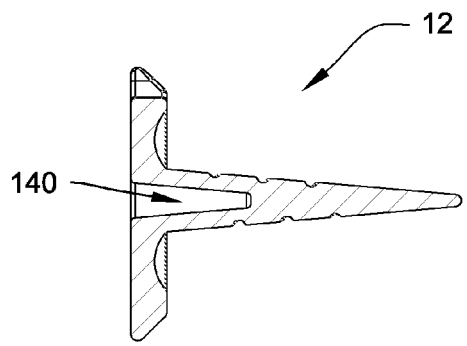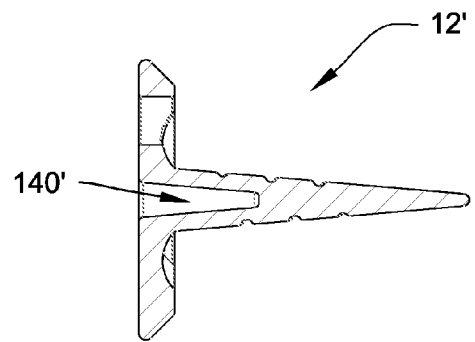
FIG. 9C  FIG. 10C

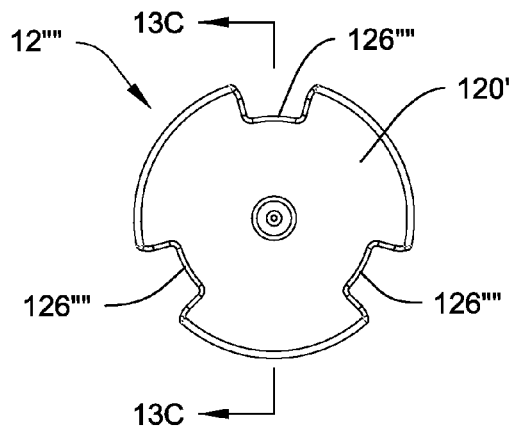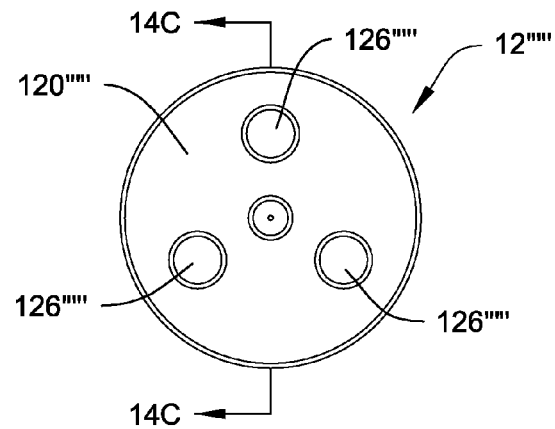
FIG. 13A　　　　　　　　FIG. 14A
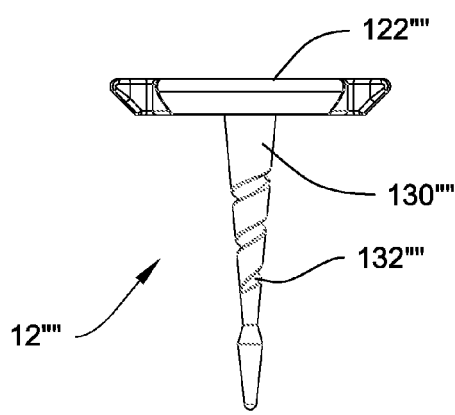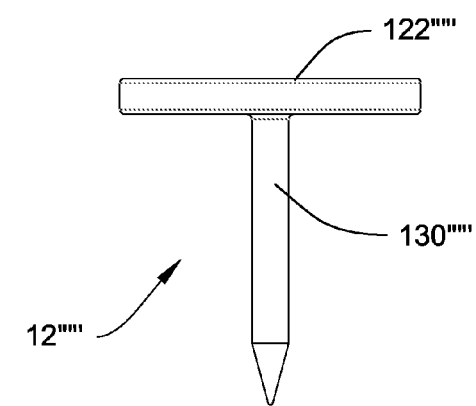
FIG. 13B　　　　　　　　FIG. 14B
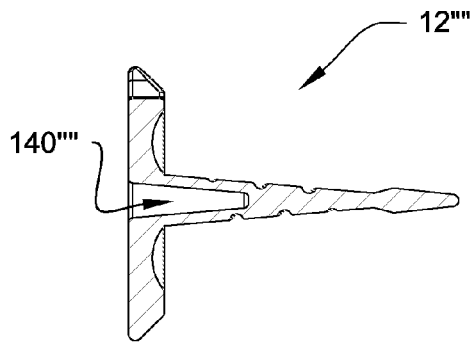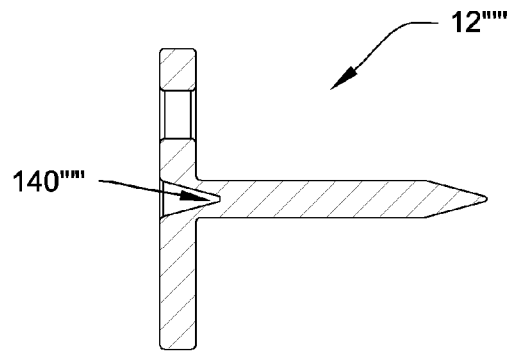
FIG. 13C　　　　　　　　FIG. 14C

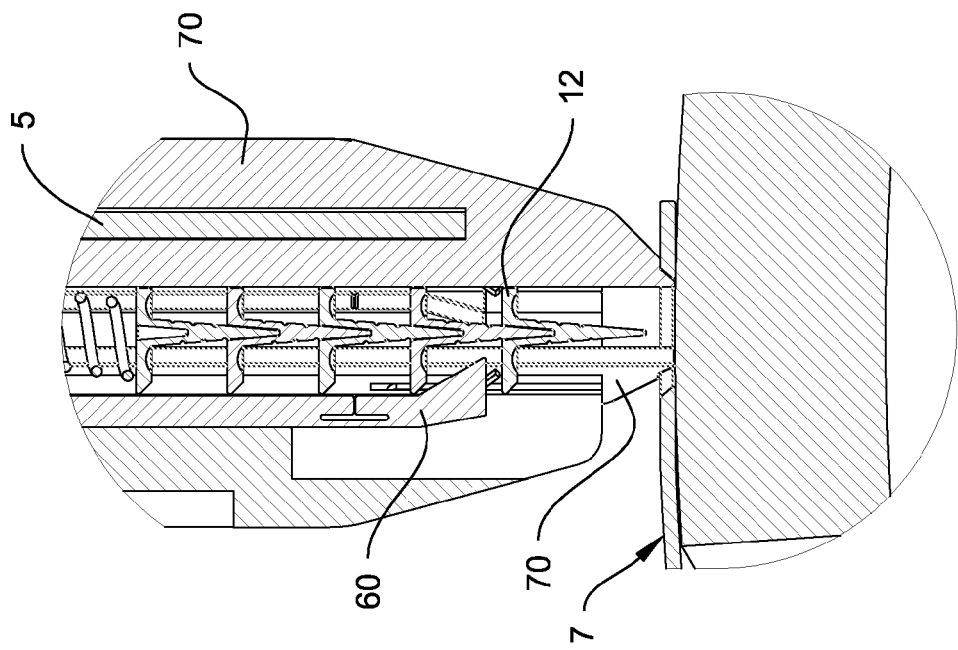
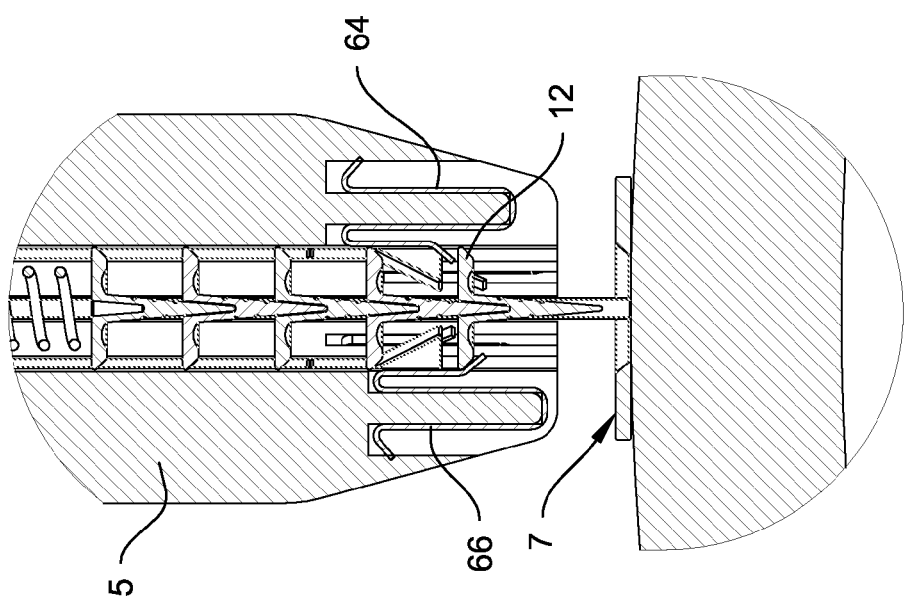
FIG. 18D
FIG. 18C

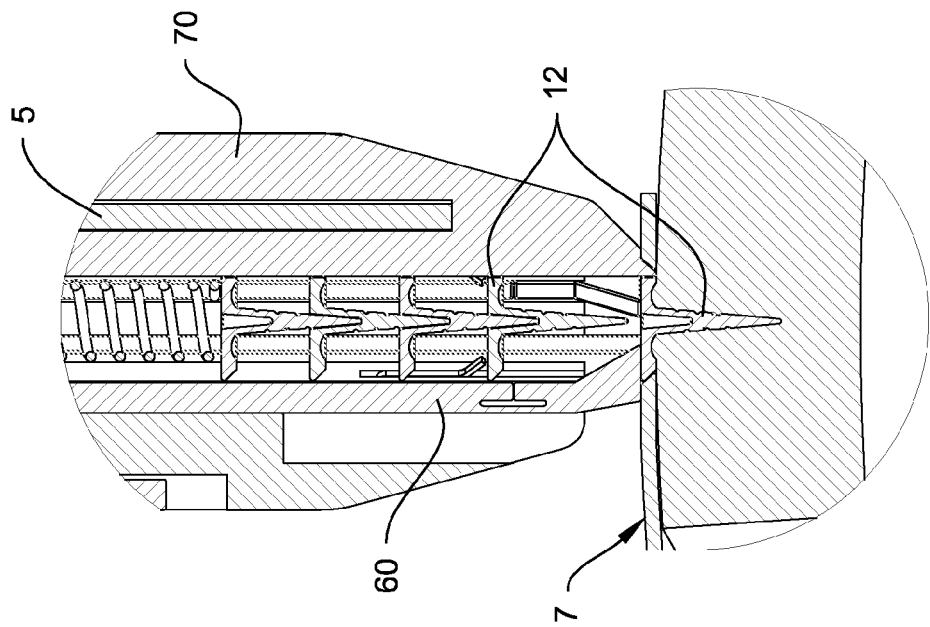
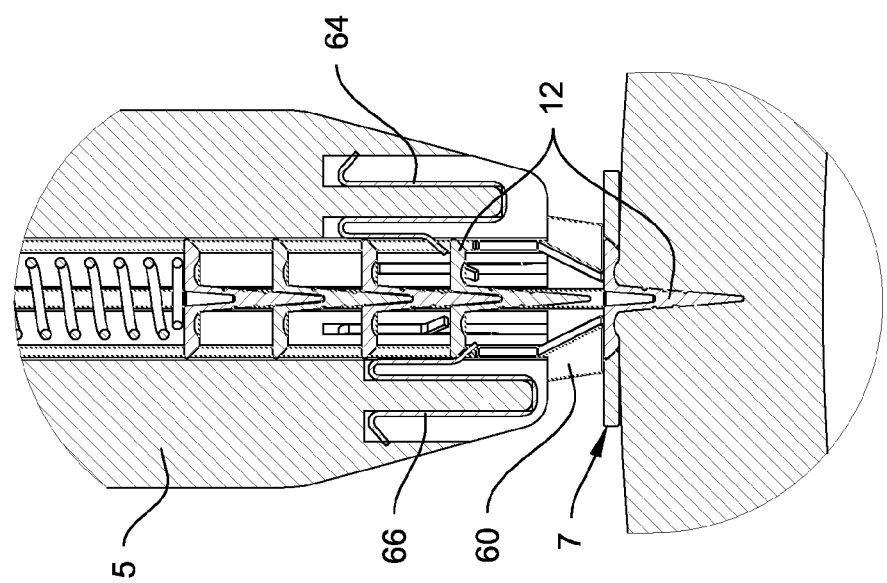

APPARATUS AND DEVICE FOR THE FIXATION OF OSTEOSYNTHESIS PLATES

CROSS REFERENCE TO RELATED APPLICATIONS

This is a non-provisional application claiming priority to U.S. Provisional Application No. 61/746,403, filed Dec. 27, 2012, which is incorporated herein by reference.

BACKGROUND ART OF THE INVENTION

The repair of separated or dislocated bone fragments or segments following bone surgery or injury requires realignment of the separated, broken, or dislocated fragments or segments and subsequent secure fixation for promoting proper natural rejoinder, of these bone fragments or segments, e.g. by osteosynthesis.

It is therefore desirable to accomplish as completely as possible an immobilization of the fracture or osteotomy site. This involves the stabilization of affected bone segments relative to each other and in relation to the surrounding bone structure. The aim of fixation of adjacent bone portions is to immobilize the fracture or osteotomy site in order to promote localized bone growth in the natural repair of the separation.

One example of an area in which such procedures are desirable is in the refixation of large area bone segments of the skull cap in neurosurgical and craniofacial operations on or through the vault of the human skull.

Another example is in the surgical treatment of craniofacial abnormalities, wherein one or more bone segments of the skull cap may be removed and reappointed to achieve a desired cosmetic result before refixation in a displaced position relative to the surrounding bone. These operations serve to correct malformations of the skull cap which are present at birth, such operations are often performed during the infancy of the patient.

At the end of such procedures, the previously removed bone fragment or fragments are repositioned into their original locations, or in different desired locations.

Known methods for providing fixation between adjacent bone portions have included the use of metallic plates of varying configurations (osteosynthesis plates), which are secured across osteotomies or fracture sites by metallic bone screws inserted with a screwdriver.

The typical prior-art apparatus and device used for the fixation of osteosynthesis plates is a screwdriver and self-tapping screw. Because the implementation of this apparatus and device is user dependent, users may easily strip out bone tissue causing the screw to no longer secure the plate to the bone or misalign the screw head with respect to the pre-drilled hole in the plate, creating a sharp edge and possible dermis irritation. The loading of the screw onto the screwdriver and the tightening process is time consuming. Screws are loaded by hand, one at a time, and are often lost and must be found before skin closure. Two drivers are typically utilized alternately to reduce screw loading delay time.

A need therefore exists for an alternative fastening device for plate/bone fixation, such as a self-centering apparatus pre-loaded with fasteners that do not strip out bone tissue or require the drilling of pilot holes. This device would save considerable time by eliminating screw loading/driving; it would also eliminate re-sterilization concerns and improve surgical outcomes.

SUMMARY

Many shortcomings in the prior art are overcome by the novel devices and methods disclosed herein, including a driving apparatus and fastener for attaching osteosynthesis plates to bone surfaces to facilitate bone stabilization/mending necessitated by traumatic injury, explorative, reconstructive, cosmetic, and/or other surgery.

The apparatus can hold one or more fasteners. The apparatus is visually guided and inserted into a pre-defined hole of an osteosynthesis plate. The user holds the apparatus generally perpendicular to the plate and presses the apparatus against the plate. The apparatus will automatically and rapidly drive one fastener through the pre-defined hole of the plate and into a bone, securing the plate to the bone. The apparatus automatically sequences the next fastener.

A preferred fastener comprises a shaft with a piercing tip connected perpendicular to a head with portions of the head having a perimeter greater than or outside the perimeter of the shaft. The head surface opposite the shaft can comprises a feature, such as a cavity, to accommodate the mating/nesting of the shaft of a subsequent fastener for the purposes of stacking.

In certain embodiments the fastener comprises features that will allow the bone tissue to capture and retain the fastener into the bone.

In certain embodiments the fastener comprises a spiral groove feature allowing the device to be rotated and easily removed from the bone.

In certain embodiments the fastener comprises a cavity for displaced bone tissue to gather.

In certain embodiments the fastener head comprises an outward taper or inward taper, or any combination thereof.

The cross section of fastener shaft can comprise a round, square, oval, rectangle, star or any other desired profile, or any combination thereof.

In certain embodiments the fastener head comprises an alignment feature to guide the fastener as it advances through the apparatus into the bone.

In certain embodiments the fastener comprises a bioabsorbable material.

In certain embodiments the fastener may be radiopaque.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 3 is a section view of a body sleeve.
FIG. 4 is a section view of a hammer.
FIG. 5A is a top-down view of a hammer sleeve.
FIG. 5B is a side view of a hammer sleeve.
FIG. 5C is a bottom-up view of a hammer sleeve.
FIGS. 9A, 10A, 11A, 12A, 13A and 14A are each a top-down view of a different, preferred nail embodiment.
FIGS. 9B, 10B, 11B, 12B, 13B and 14B are each a side view of a different, preferred nail embodiment.

FIGS. 9C, 10C, 11C, 12C, 13C and 14C are each a side section view of a different, preferred nail embodiment taken along the corresponding lines indicated in FIGS. 9A, 10A, 11A, 12A, 13A and 14A.

FIGS. 16C-16D, 17C-17D, 18C-18D, 19C-19D, 20C-20D, 21AC-21D and 22C-22D are each an enlarged partial section view of an affixiation tool at a different stage of operation, detailing a muzzle tip and components indicated in corresponding A and B Figures.

DETAILED DESCRIPTION OF THE PREFERRED EMBODIMENTS

Figure 1:
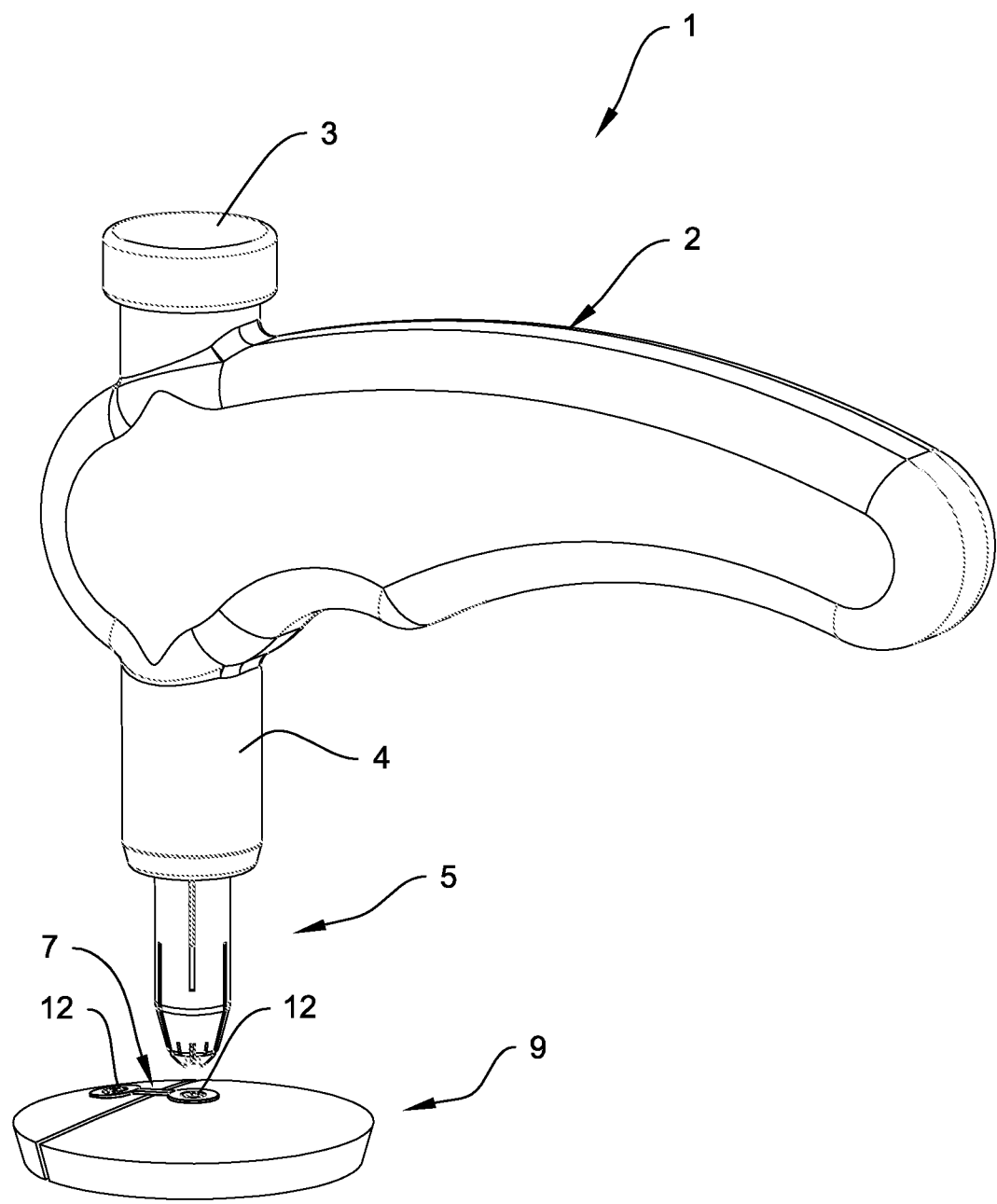
FIG. 1 is a perspective view of an affixation tool.

FIG. 1 is a perspective view of an affixation tool 1. Affixation tool 1 is configured to deliver one or more a fastener 12 to secure a plate, implant, artificial organ, or the like to a suitable tissue of a patient, such as a bone. Affixation tool 1 generally comprises handle 2, body cylinder 4, cap 3, and muzzle 5. Handle 2 and body cylinder 4 are preferably molded from a polymer such as polypropylene. Handle 2 is preferably configured to be easily grasped by a user (not shown). Muzzle 5 is configured to engage plate 20 to facilitate precise placement of an a fastener 12 to secure plate 20 to bone 30.

Figure 2A:
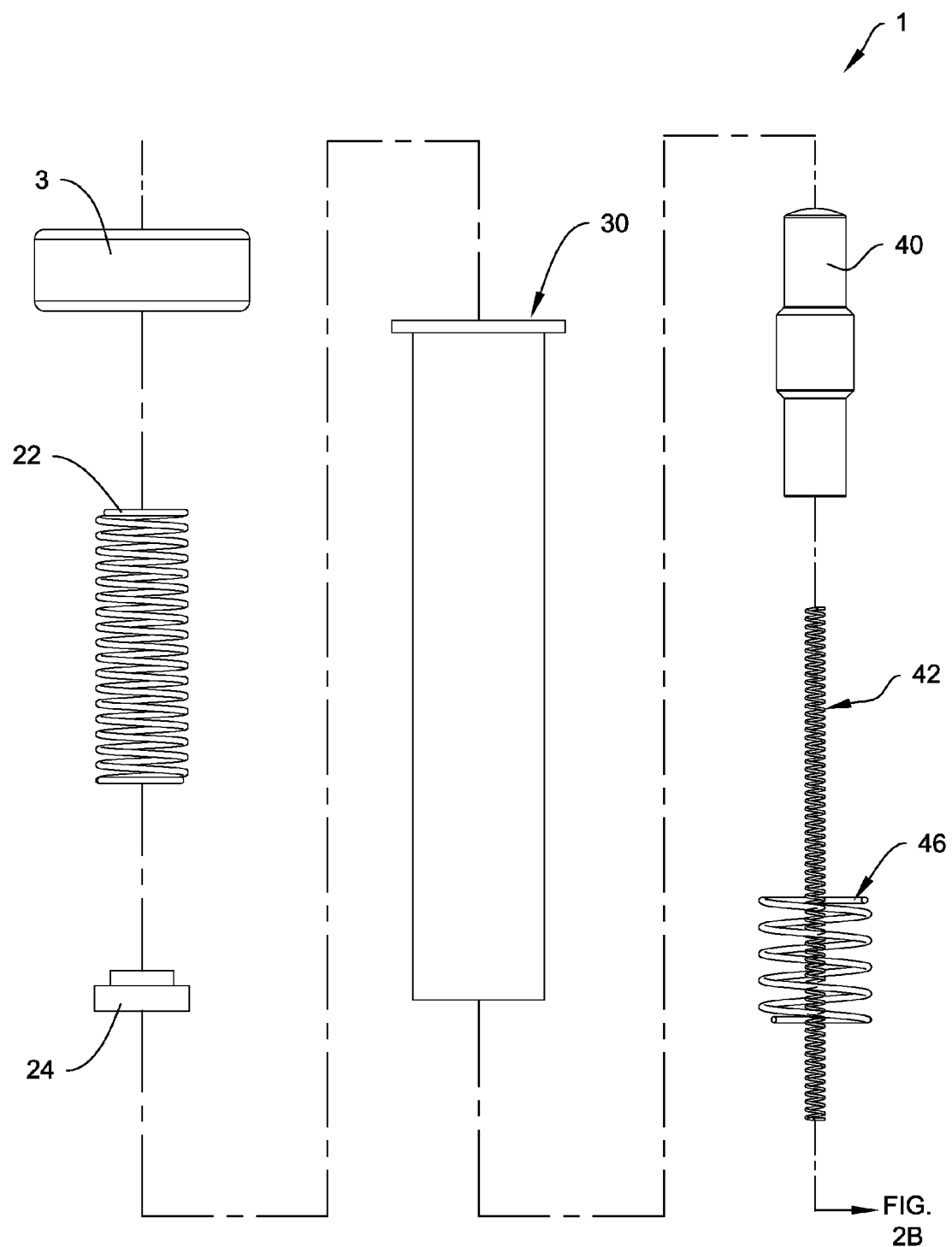
FIGS. 2A-2C is an exploded view of an affixation tool.
Figure 2B:
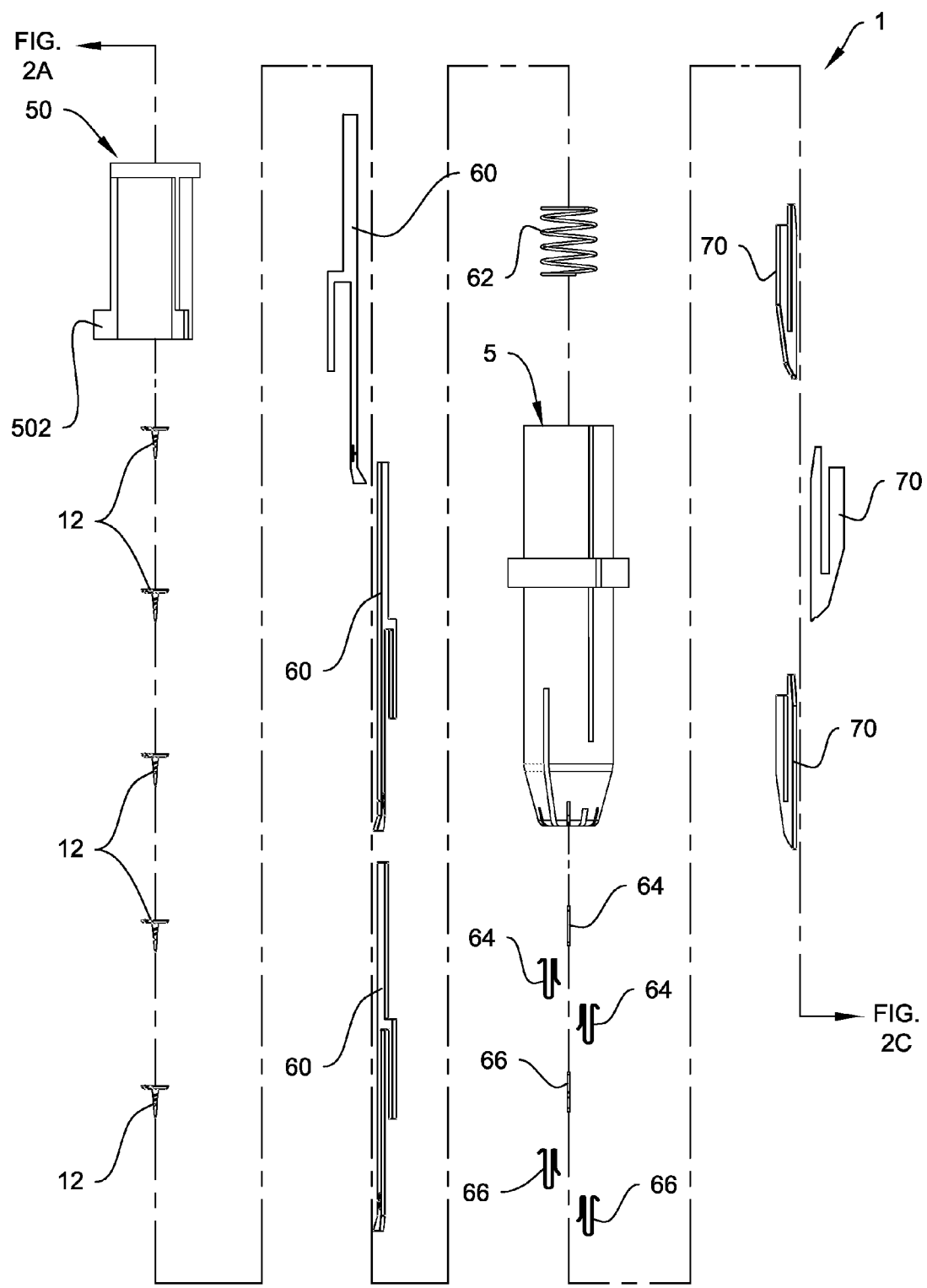
Figure 2C:
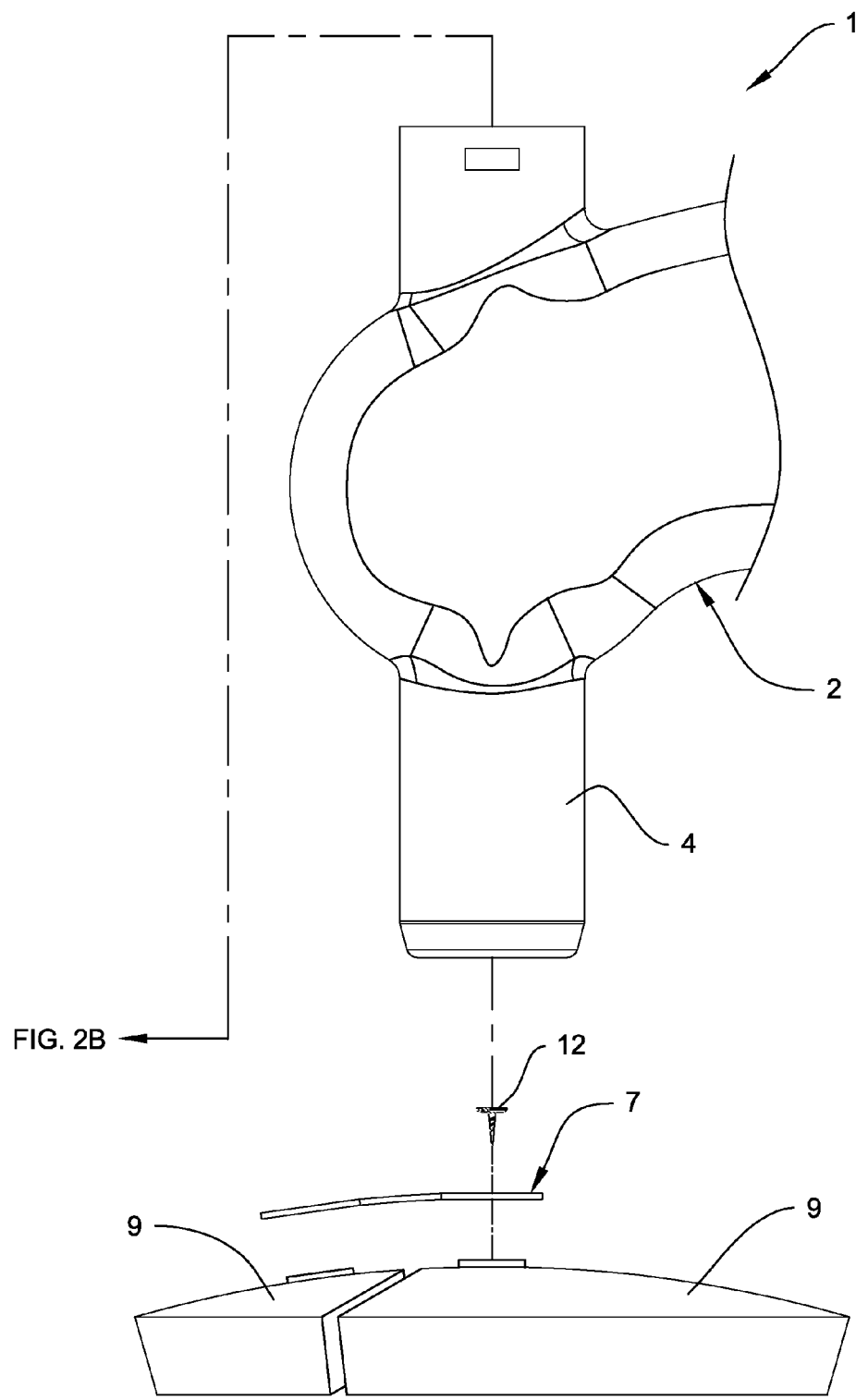

FIGS. 2A-2C provide an exploded view of affixation tool 1, illustrating various internal components. Cap 3 is configured to engage body cylinder 4 and contain other internal components. Below (in this description, the terms "above" or "behind" mean toward cap 3 while the terms "below" or "forward" mean toward muzzle 5) cap 3 are hammer spring 22, hammer plate 24, and body sleeve 30. Body sleeve 30 is further described in connection with FIG. 3. When affixation tool 1 is assembled, hammer spring 22 is compressed between cap 3 and hammer plate 24 within body sleeve 30.

Below hammer plate 24 is hammer 40. Hammer 40 is described in more detail in connection with FIG. 4. Hammer plate 24 and hammer spring 22 apply a downward force against hammer 40. However, as will be discussed more thoroughly below, hammer 40 is prevented from moving forward until affixation tool 1 is activated.

Counterspring 42 is positioned between muzzle 5 and hammer 40, extending partially through hammer 40. Counterspring 42 aids in resetting hammer 40 to its original position after an fastener 12 has been deployed. Counterspring 42 also provides a canting tendency to hammer 40.

Forward of hammer 40 is hammer sleeve 50. Hammer sleeve 50 is generally cylindrical and concentric with body sleeve 30. Body reset spring 46 is preferably positioned around hammer sleeve 50 and provides a force between hammer sleeve 50 and body sleeve 30.

Referring to FIG. 2B, also forward of hammer 40 are one or more hammer fingers 60. Hammer fingers 60 are described in more detail in connection with FIG. 6A-6B. Hammer fingers 60 are preferably configured to be positioned partially within hammer sleeve 50 and extend downwardly therefrom. A finger reset spring 62 preferably surrounds a portion of hammer fingers 60 and is configured to provide a force between hammer fingers 60 and muzzle 5. When affixation tool 1 is assembled and loaded, one or more fasteners 12 are disposed adjacent to or between hammer fingers 60.

A forward end of muzzle 5 preferably comprises one or more first sequencing springs 64, one or more second sequencing springs 66, and one or more positioning rails 70.

Referring to FIG. 2C, all of the above-described components of affixation tool 1 are preferably enclosed in and/or attached to body cylinder 4. Also visible in FIG. 2C are plate 20 and bone 30.

Referring to FIG. 3, body sleeve 30 is a tube comprising a generally-cylindrical outer wall 302 with an annular lip 304 surrounding its upper end. An inner wall 310 is also generally-cylindrical but preferably includes several features. First, a hammer orientation ring 312 is preferably defined on inner wall 310. Hammer orientation ring 312 has an inner diameter smaller than the inner diameter of portions of inner wall 310 above and below hammer orientation ring 312. Hammer orientation ring 312 preferably comprises a plate stop 314 configured to engage hammer plate 24. Hammer orientation ring 312 also preferably comprises orientation ramp 316 configured to engage hammer 40. Second, a reset notch 320 is defined in inner wall 310. Reset notch 320 is preferably configured to engage body reset spring 46. Alternatively, an annular ring (not shown), a plurality of internally-directed tabs or rungs, or other devices could be used in place of reset notch 320.

Referring to FIG. 4, hammer 40 is generally cylindrical but comprises a plurality of segments with differing diameters. A first segment 410 preferably comprises a partially-spherical upper surface 412 and has a first outer diameter. A second segment 420 has a second outer diameter, preferably larger than the first outer diameter. A third segment 430 has a third outer diameter preferably smaller than the second outer diameter. The third outer diameter can be equal to first outer diameter. A first angular ramp 442 is defined between first segment 410 and second segment 420. A second angular ramp 444 is defined between second segment and third segment 430. First angular ramp 442 and second angular ramp 444 each preferably have an angle between 30 degrees and 70 degrees with respect to a centerline of hammer 40. However, first angular ramp 442 and second angular ramp 444 can have different angles and will angle in opposite directions.

A spring cavity 452 is defined along at least a portion of central axis of hammer 40 and is preferably configured to receive a portion of counterspring 42.

FIGS. 5A-5C further illustrate hammer sleeve 50. Hammer sleeve 50 is generally cylindrical and comprises one or more edge ribs 501 extending longitudinally down an exterior sleeve wall 503. Spring tabs 502 extend laterally from edge ribs 501 near a bottom end of edge rib 501. A hammer rim 504 surrounds the top edge. Spring tabs are configured to engage body reset spring 46 so that body reset spring 46 provides force between hammer sleeve 50 and body sleeve 30.

Figure 6A:
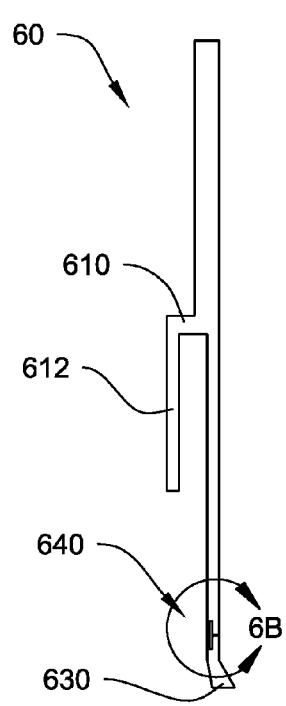
FIG. 6A is a side view of a hammer finger.

FIG. 6A is a larger view of a hammer finger 60. Hammer finger 60 is preferably a generally-flat, elongate structure preferably comprising a metal such as stainless steel. A spring shelf 610 extends laterally from hammer finger 60 at around its midpoint. Spring shelf 610 is configured to engage finger reset spring 62. An alignment guide 612 extends forwardly from an outward end of spring shelf 610. Alignment guide 612 is preferably configured to engage guide notches 740 defined in muzzle 5. A hammer tip 630 is defined on the forward end of hammer finger 60. Hammer tip is preferably angled inwardly with respect to the rest of hammer finger 60.

Figure 6B:
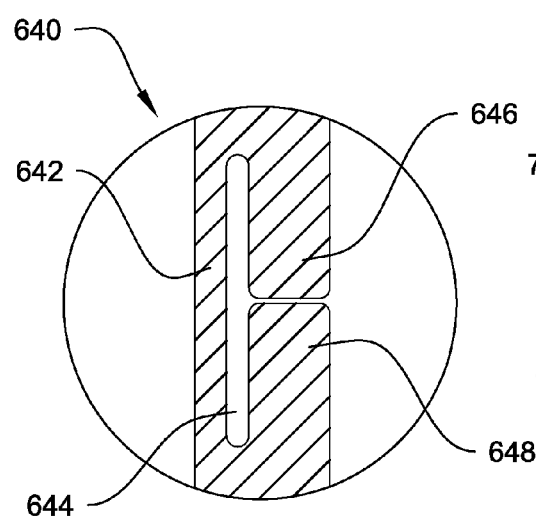
FIG. 6B is an enlarged view of a partial section view of a hammer finger.

Referring to FIG. 6B, above but preferably near hammer tip 630, is a tip spring 640. Tip spring 640 comprises a leaf spring 642 along an outer edge of hammer finger 60, a spring cavity 644 immediately inward of leaf spring 642, and an upper peninsula 646 and lower peninsula 648. Upper peninsula 646 and lower peninsula 648 are preferably configured to contact or almost contact each other when hammer finger 60 is in a relaxed position. Tip spring 640 allows hammer tip 630 to be pushed outward from its relaxed position when an outward force is applied, but offers significantly higher resistance to inward movement of hammer tip 630, thereby allowing hammer tip 630 to impart significant force to an fastener 12.

Figure 7A:
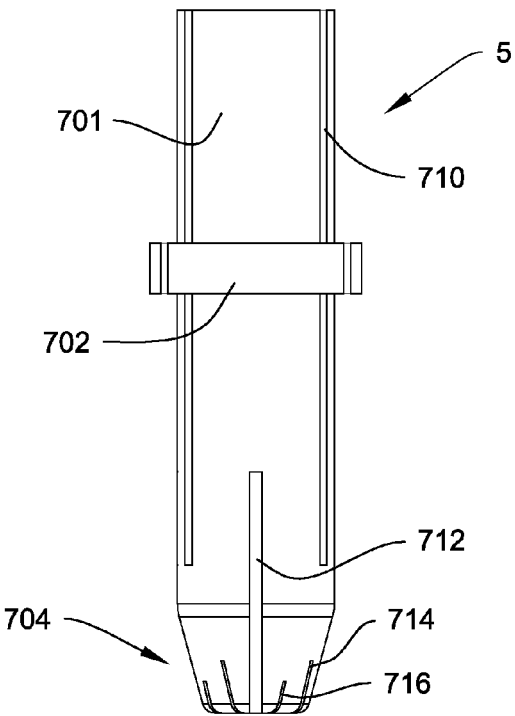
FIG. 7A is a side view of a muzzle of an affixation tool.

FIG. 7A is a closer view of muzzle 5. The exterior of muzzle 5 is generally cylindrical muzzle wall 701 with an annular muzzle shelf 702 and a frusto-conical muzzle tip 704 at the bottom. One or more guide notch 710 is preferably defined in muzzle wall 701 from the top to a point above muzzle tip 704. Additionally, one or more rail notch 712 is defined in muzzle wall 701 from muzzle tip 704 to a point above the bottom of guide notch 710. Further additionally, one or more upper advancement spring notch 714 and lower advancement spring notch 716 are defined in muzzle tip 704.

Figure 7B:
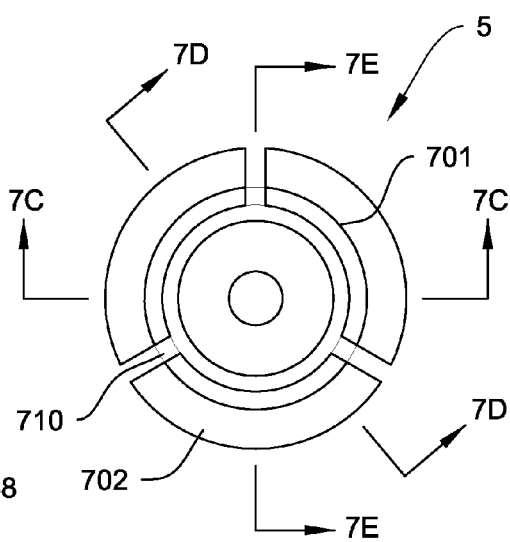
FIG. 7B is a top-down view of a muzzle of an affixation tool.

FIG. 7B is a top-down view of muzzle 5.

Figure 7C:
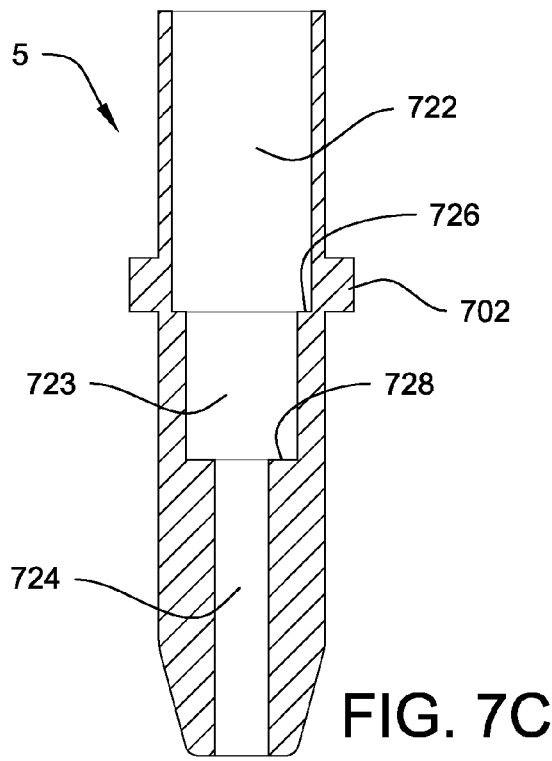
FIGS. 7C-7E are section views of a muzzle of an affixation tool taken along the corresponding lines indicated in FIG. 7B.

FIG. 7C is a section view of muzzle 5 taken along line 7C-7C of FIG. 7B. FIG. 7C shows a cross-section of muzzle wall 701 at a point where no notches are defined in its exterior. The interior profile of muzzle wall 701 defines an upper muzzle section 722, an intermediate muzzle section 723, and a lower muzzle section 724. Upper muzzle section 722 has a larger inner diameter than intermediate muzzle section 723. Upper muzzle section 722 and lower muzzle section 724 meet at about the same height as muzzle shelf 702 and define a hammer tube shelf 726. Intermediate muzzle section 723 has a larger inner diameter than lower muzzle section 724. Intermediate muzzle section 723 and lower muzzle section 724 meet at a point below muzzle shelf 702 and above muzzle tip 704 and define reset spring shelf 728.

Figure 7E:
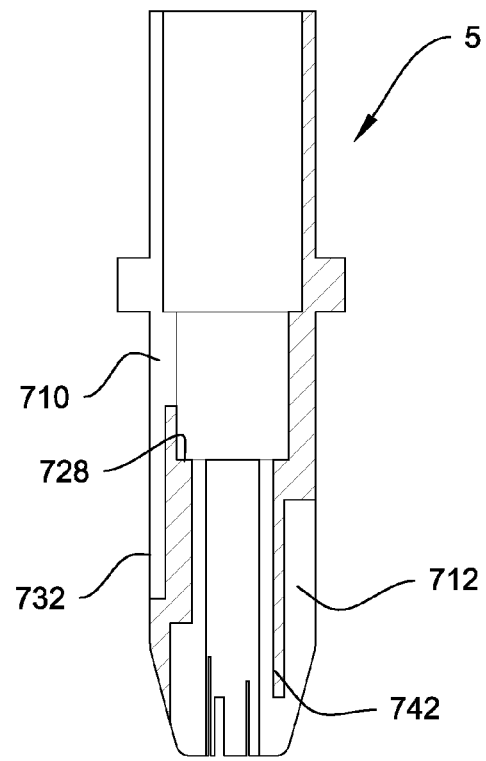
Figure 7D:
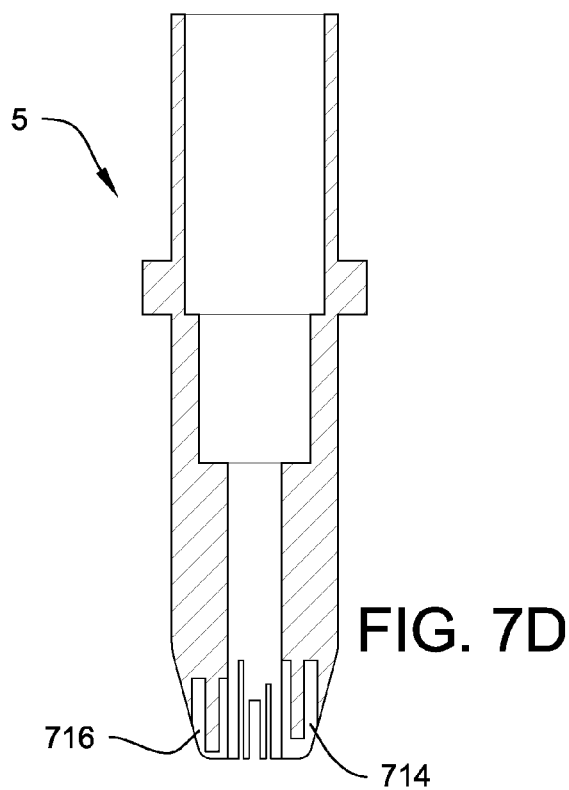

FIG. 7D is a section view of muzzle 5 taken along line 7D-7D. FIG. 7D illustrates the configuration of upper advancement spring notch 714 and lower advancement spring notch 716, which are configured to hold upper advancement spring 64 and lower advancement spring 66, respectively.

FIG. 7E is a section view of muzzle 5 taken along line 7E-7E. In FIG. 7E, guide notch 710 and rail notch 712 are visible. As shown, guide notch 710 extends completely through muzzle wall 701 from the top of muzzle 5 to a point above reset spring shelf 728. A further part of guide notch 710 extends only partially through muzzle wall 701, defining a guide channel 732. Guide channel 732 is preferably configured to engage at least a portion of alignment guide 612 of hammer finger 60.

Rail notch 712 extends up from muzzle tip 704 along both the exterior and interior of muzzle wall 701, in a generally U-shaped configuration, around a rail guide 742.

Figure 8:
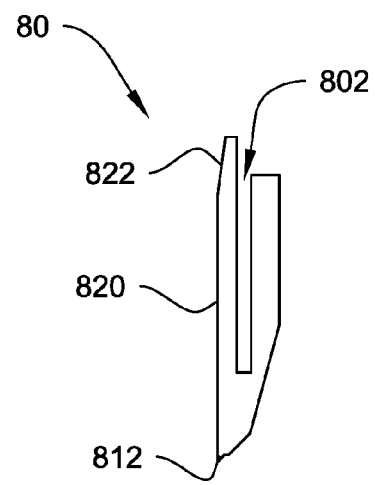
FIG. 8 is a enlarged side view of an alignment rail.

FIG. 8 is a closer view of alignment rail 80. Alignment rail 80 is preferably a flat metal piece with a guide channel 802 defined downwardly from a top edge, and a pointed rail tip 812 at a lower end. Guide channel 802 is configured to engage rail guide 742 of muzzle 5. Bottom tip 812 is preferably configured to engage a hole defined in plate 20 to ensure proper alignment of affixation tool 1 and fastener 12 with plate 20. Bottom tip 812 is preferably located on or adjacent inside edge 820 of alignment rail 80. An alignment bevel 822 is defined on the upper end of inside edge 820.

All springs composing affixation tool 1 are preferably fabricated from metals such as stainless steel, spring steel, or the like. Most other components are preferably fabricated using thermoplastic polymers, such as polypropylene, polyethylene, or the like. Fasteners are preferably between 1 mm and 0.5 mm, and more preferably, between 0.55 mm and 0.45 mm.

FIG. 9A-9C illustrate a preferred embodiment of an fastener 12. FIG. 9A is a side view of fastener 12. As shown, fastener 12 generally comprises a wider head portion 120 and a narrower shaft 130. Head portion 120 preferably comprises a flat top 122 and tapered edges 124. As illustrated in FIG. 9B, head portion 120 also preferably comprises one or more head notch 126 defined on its perimeter.

Shaft 130 is generally conical. Shaft 130 preferably includes a helical groove 132 defined on its outer surface. Helical groove 132 aids in maintaining cohesion between fastener 12 and bone 30.

As illustrated in FIG. 9C, a conical nesting cavity 140 is preferably defined in fastener 12. Nesting cavity 140 is configured to receive the forward end of shaft 130 of the next fastener 12, if one is present.

FIGS. 10A, 10B, and 10C illustrate an alternative embodiment of an fastener 12'. Fastener 12' is essentially the same as fastener 12 except that fastener 12' includes guide holes 126' in place of head notches 126.

Figure 11A:
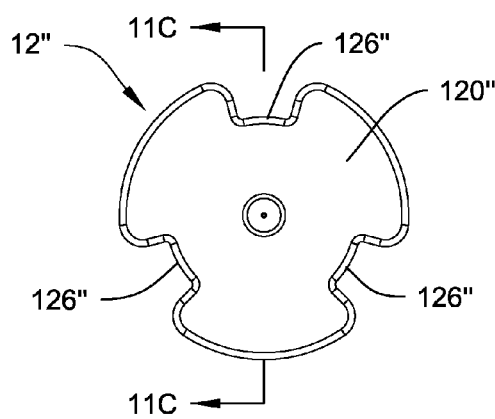
Figure 12A:
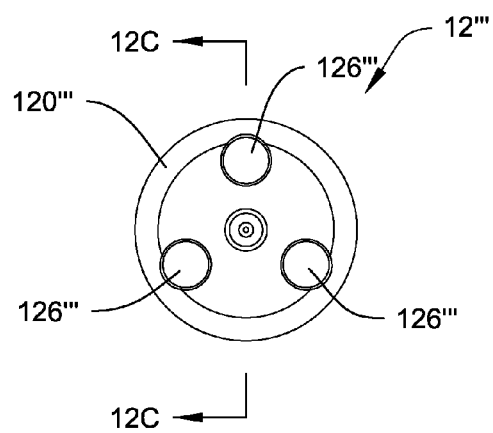
Figure 11B:
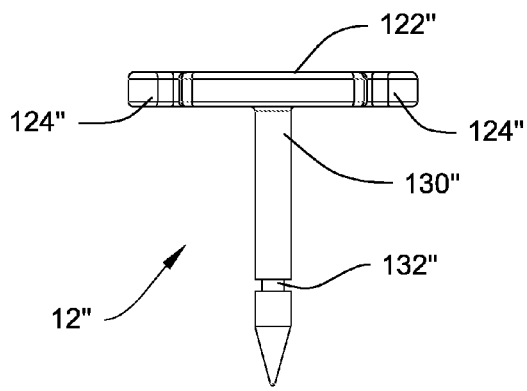
Figure 12B:
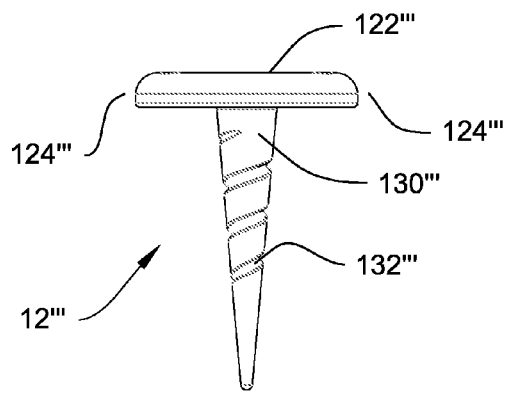
Figure 11C:
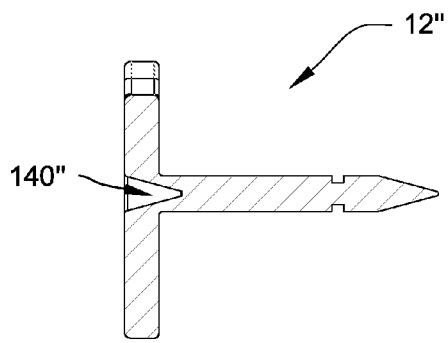
Figure 12C:
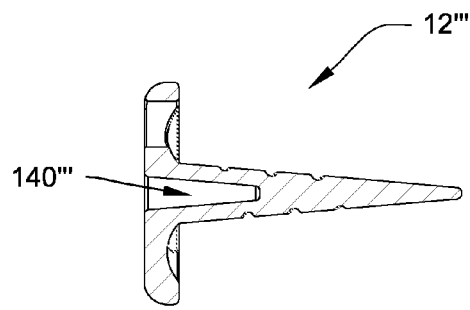

FIGS. 11A, 11B, and 11C illustrate an additional alternative embodiment of an fastener 12". Fastener 12" comprises head notches 126 similar to those of fastener 12. However, head portion 120' of fastener 12" is not tapered on its edge, and shaft 130' is only conical at its forward end. Additionally, fastener 12" comprises shaft notch 132" in place of helical groove 132, and nesting cavity 140' is substantially smaller.

FIGS. 12A-14C illustrate additional alternative embodiments of a fasteners.

Figure 15:
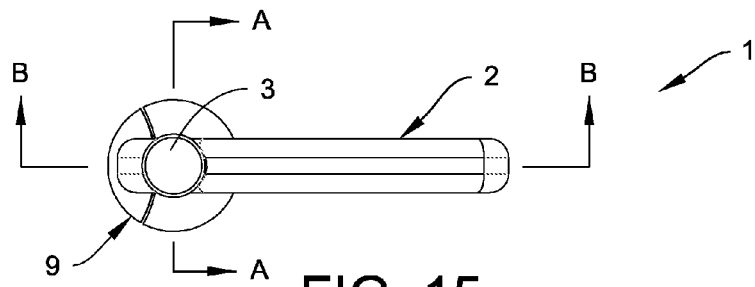
FIG. 15 is a top-down view of an affixiation tool.
Figures 16A, 16B:
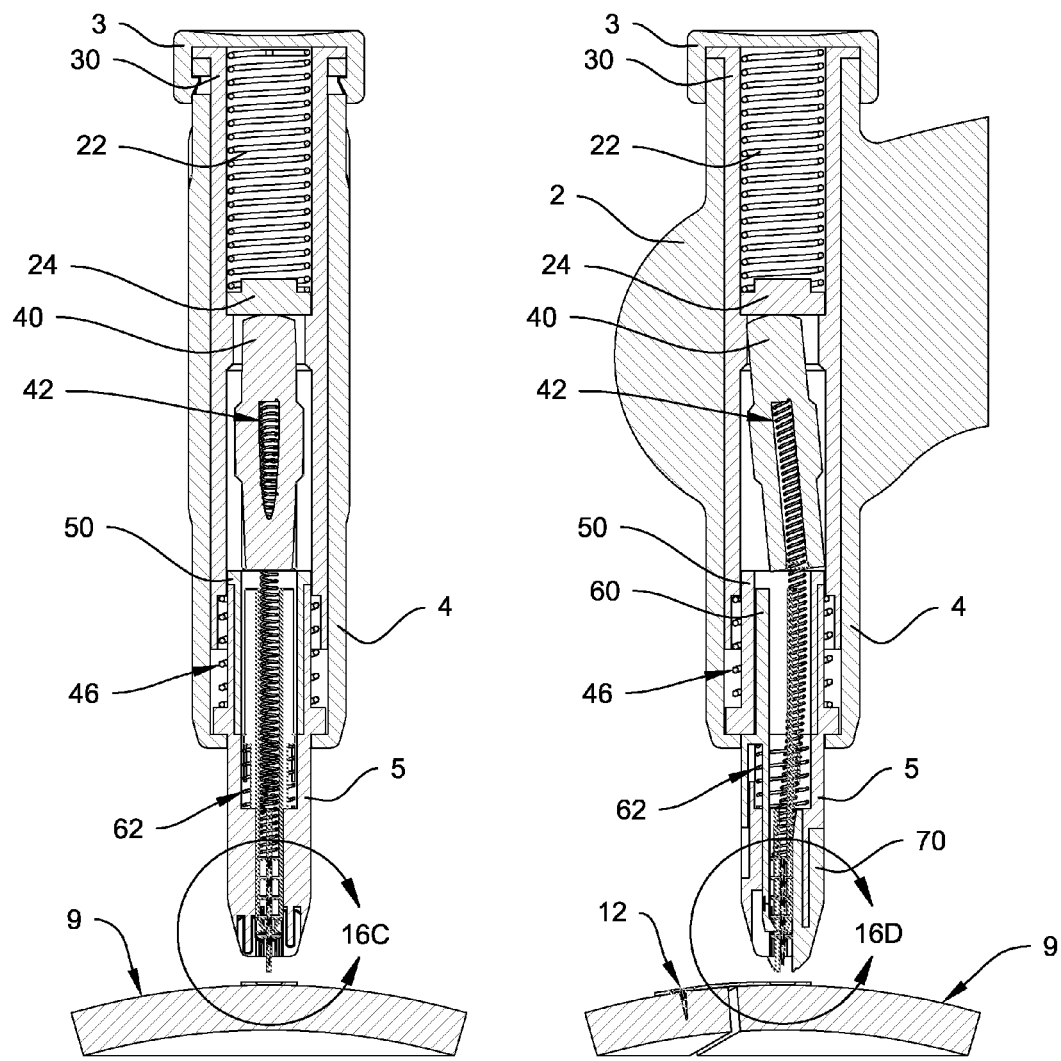
FIGS. 16A-16B, 17A-17B, 18A-18B, 19A-19B, 20A-20B, 21A-21B and 22A-22B are each a partial section view of an affixiation tool at a different stage of operation, taken along the corresponding lines indicated in FIG. 15.
Figure 16D:
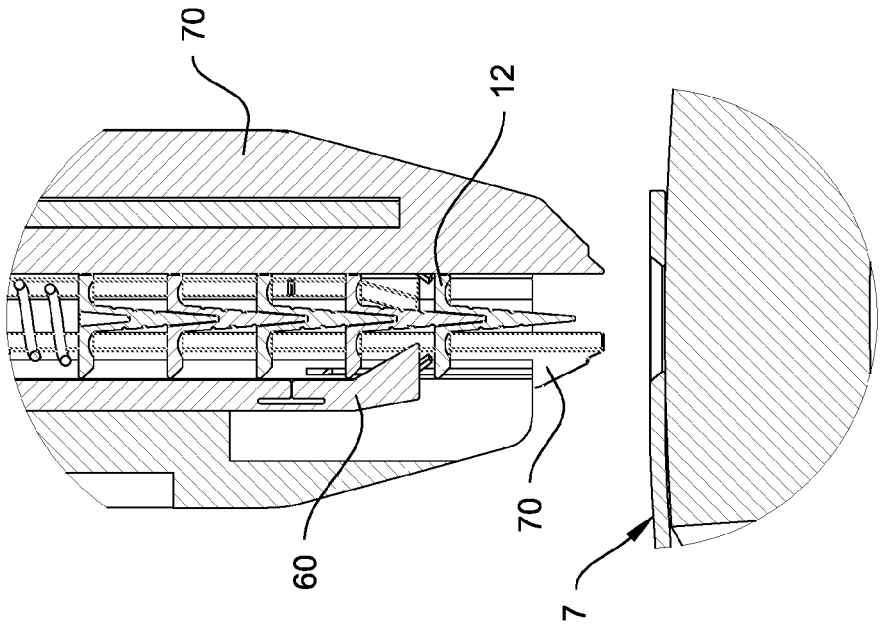
Figure 16C:
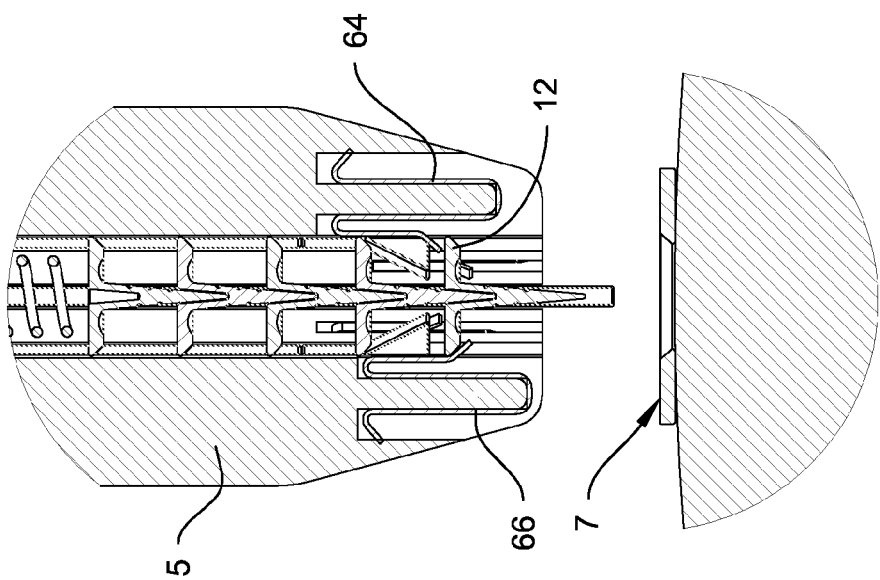
Figure 17A:
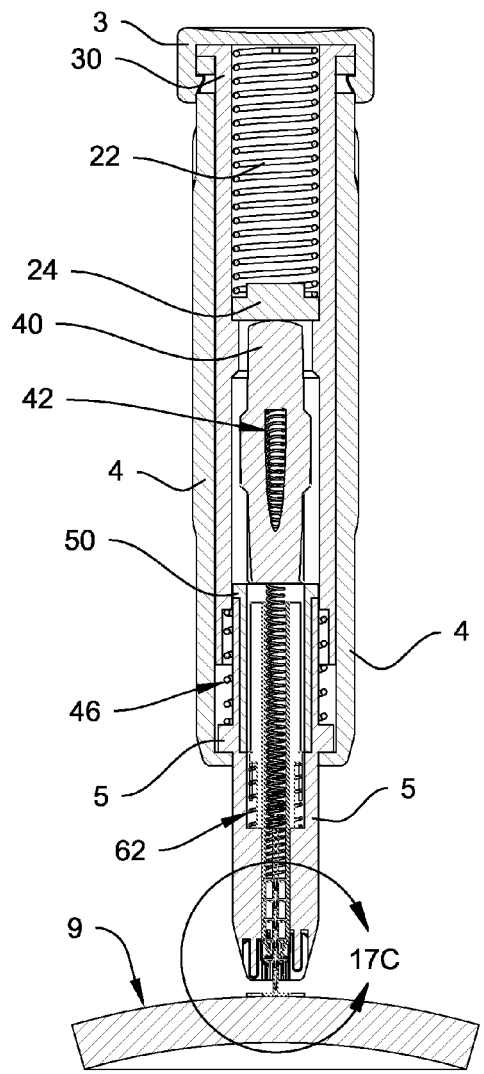
Figure 17B:
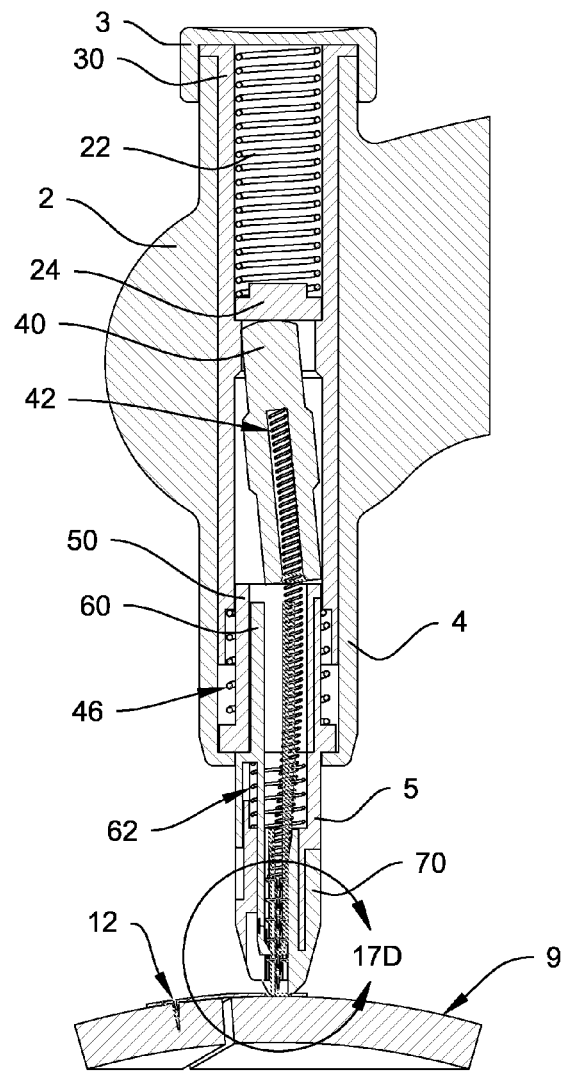
Figure 17D:
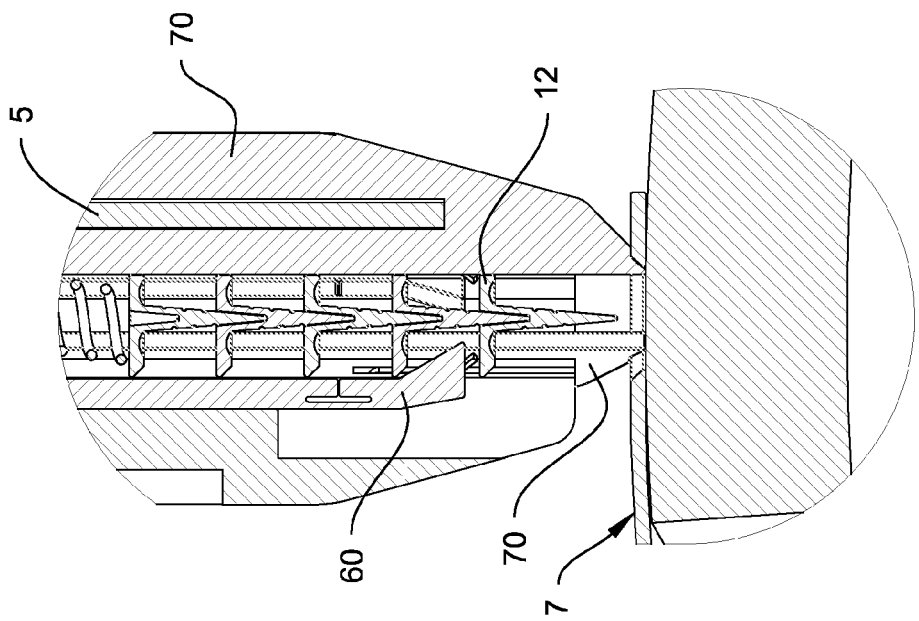
Figure 17C:
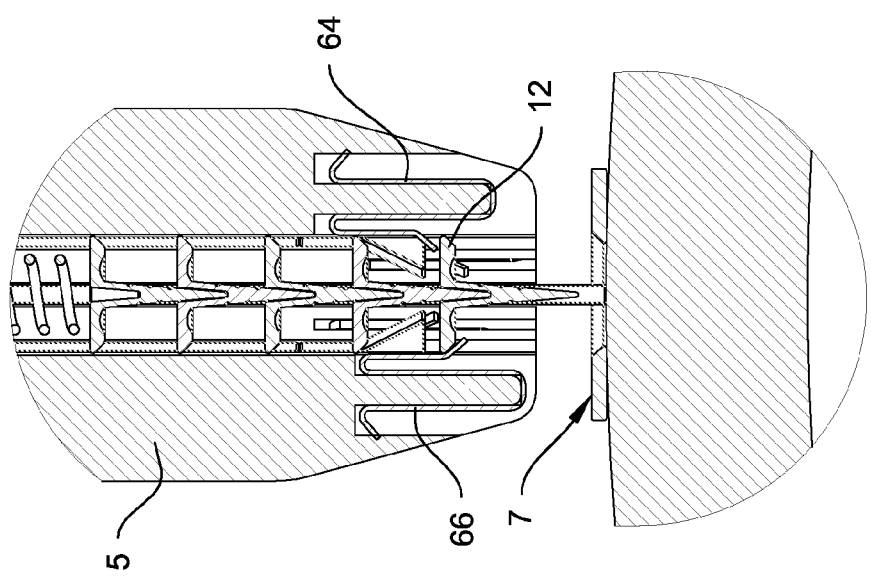
Figure 18A:
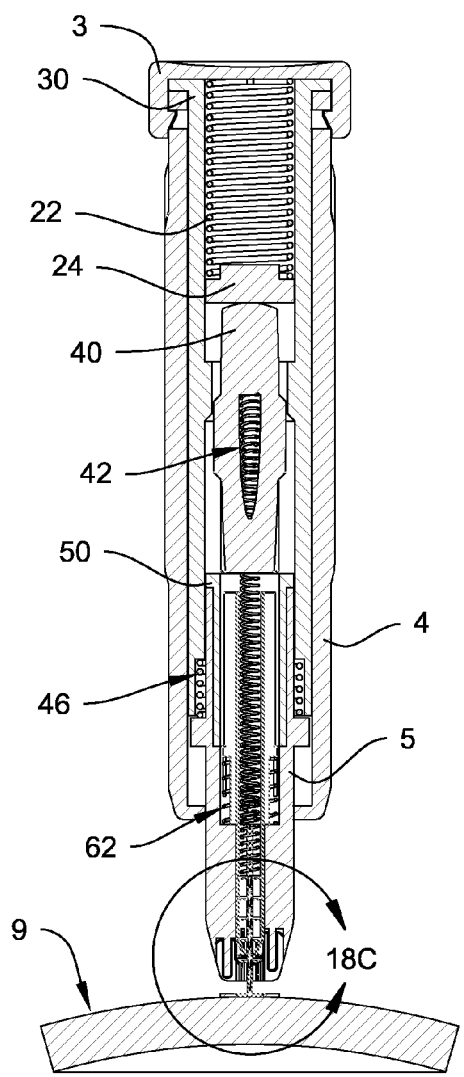
Figure 18B:
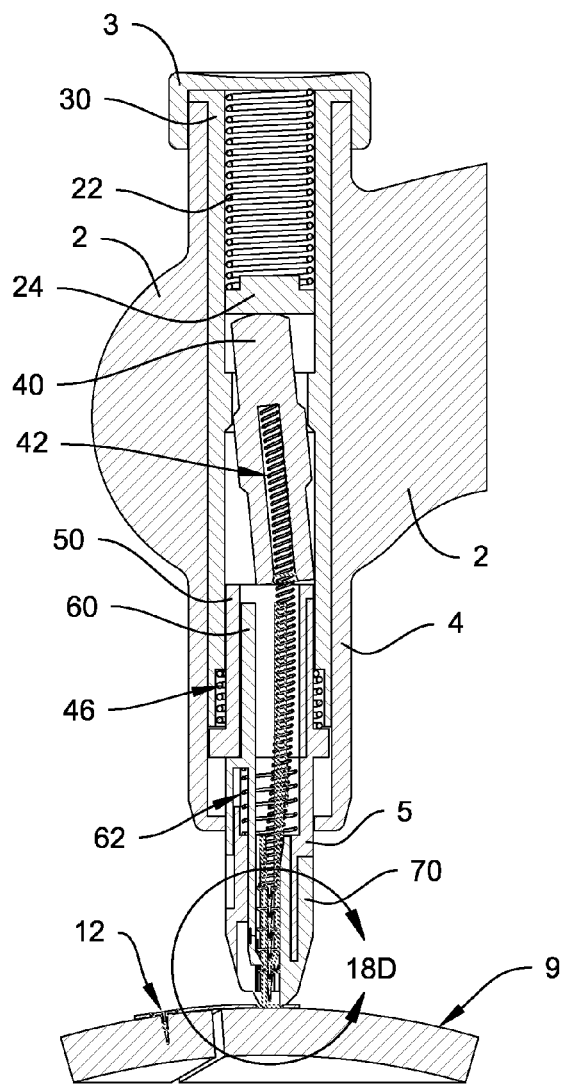
Figure 19A:
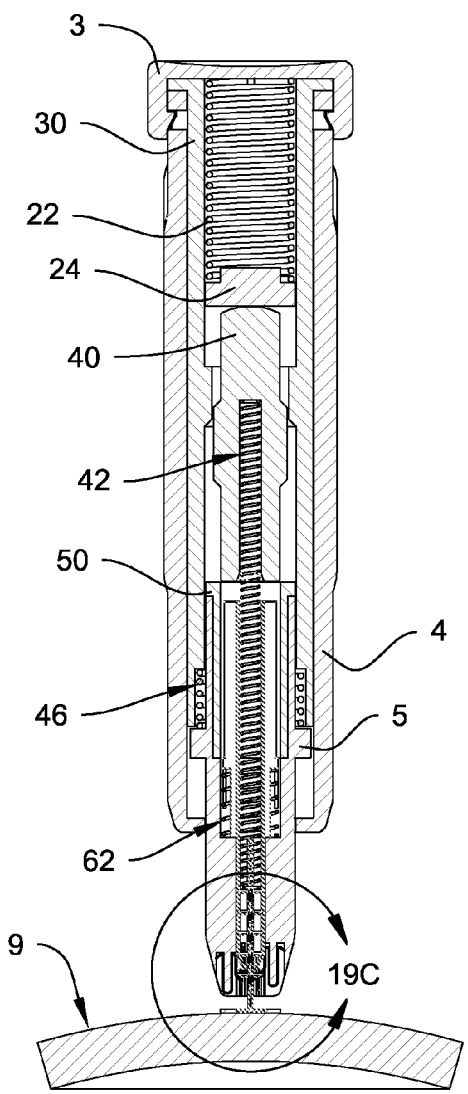
Figure 19B:
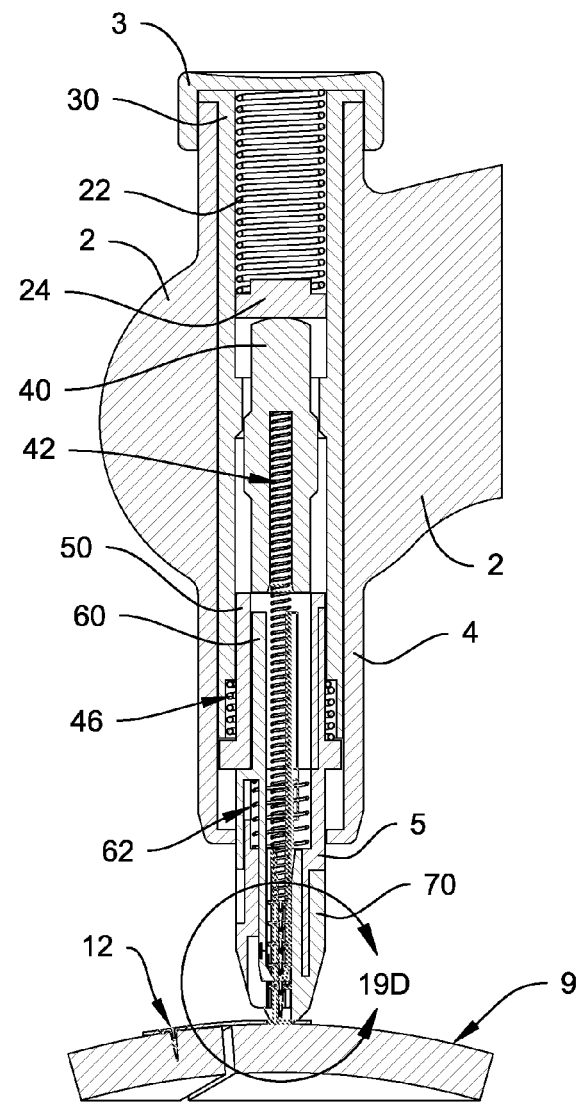
Figure 19D:
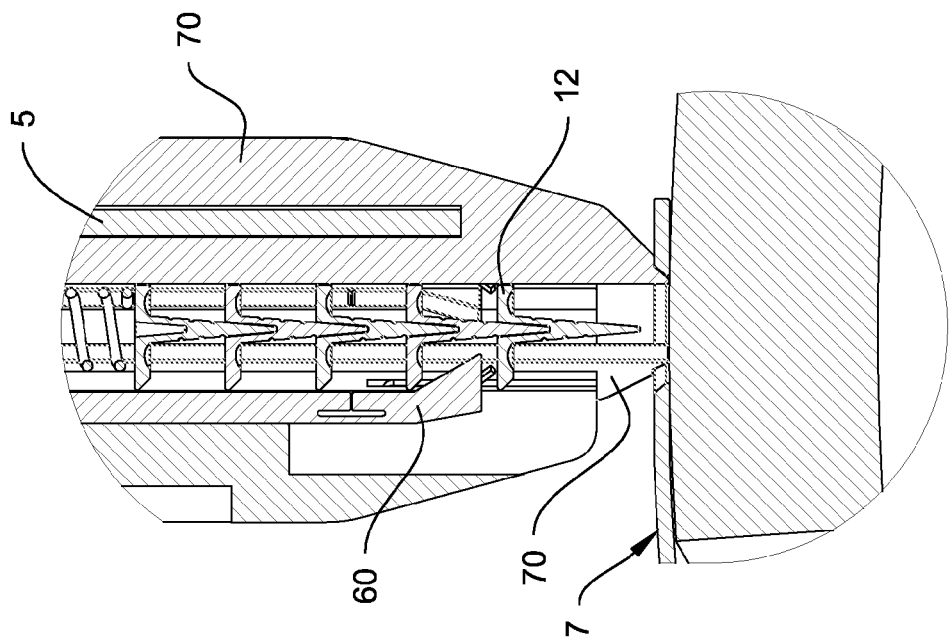
Figure 19C:
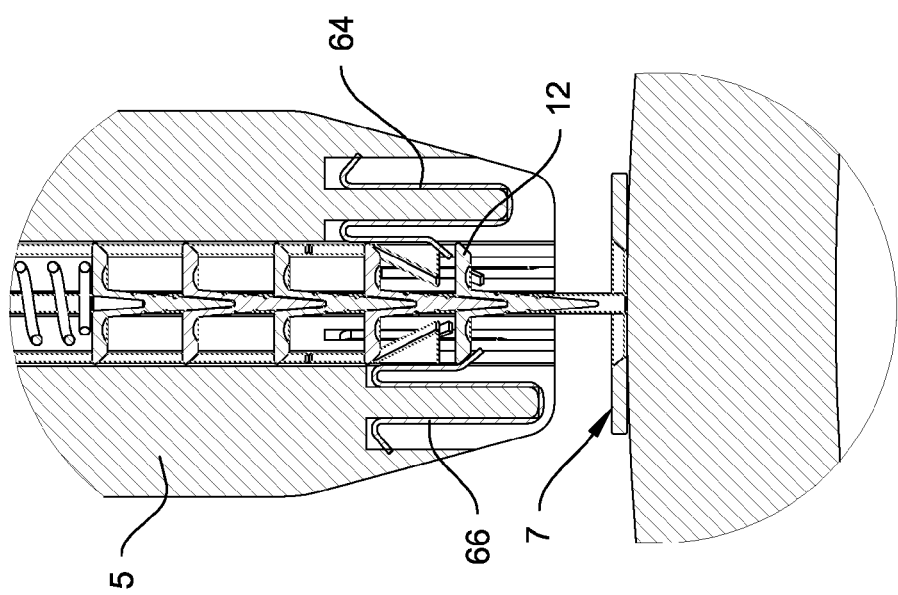
Figure 20A:
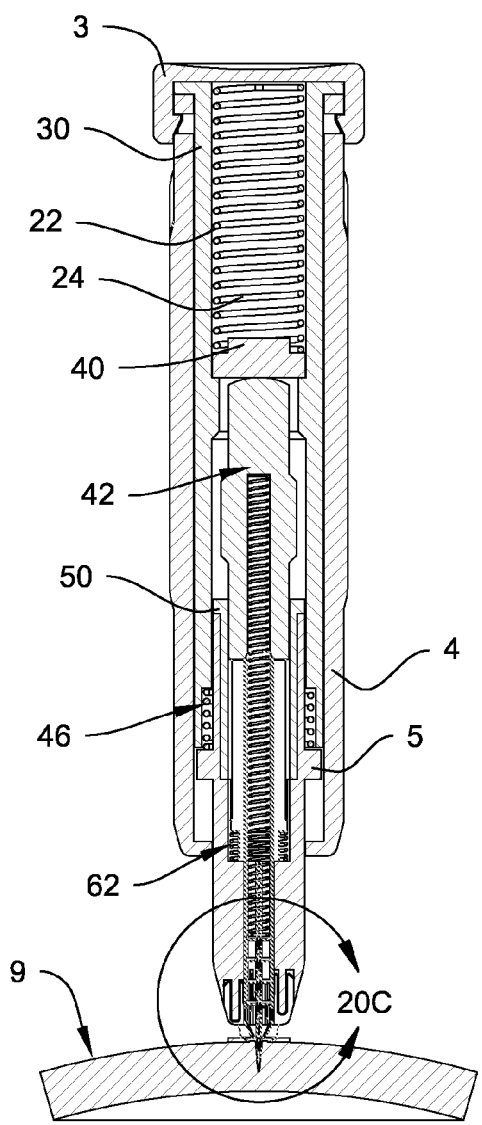
Figure 20B:
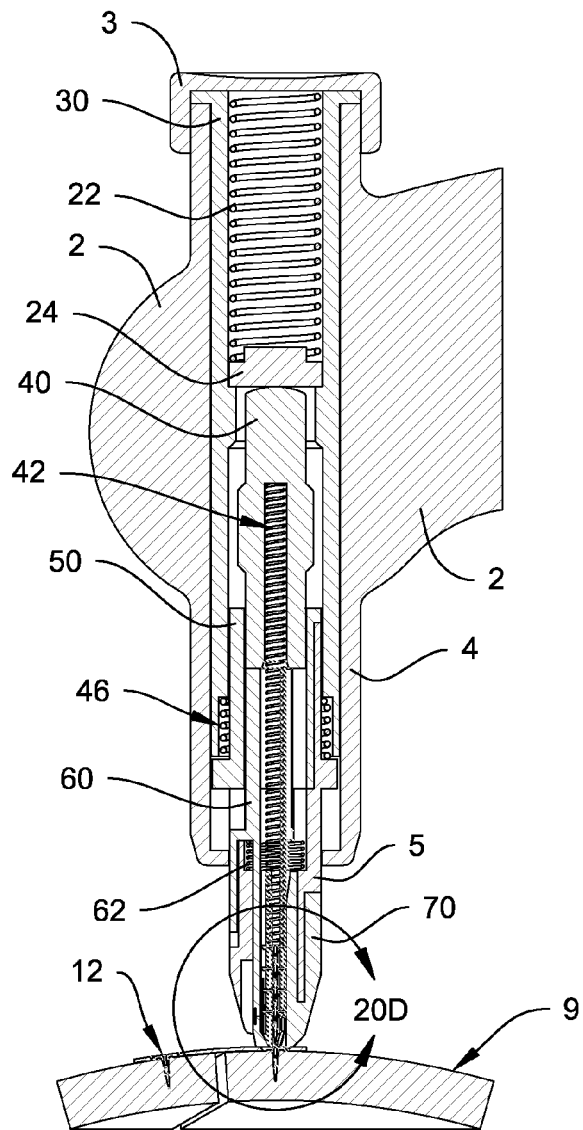
Figure 21A:
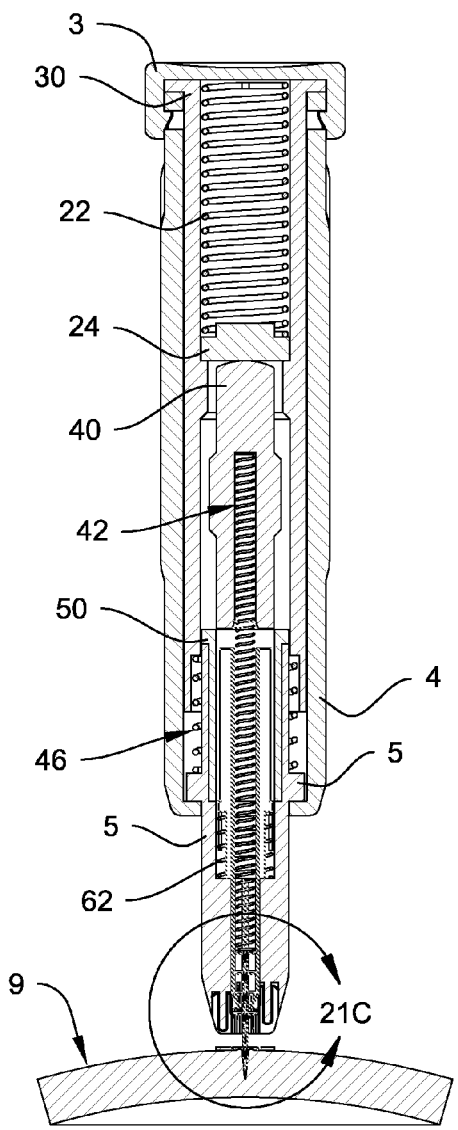
Figure 21B:
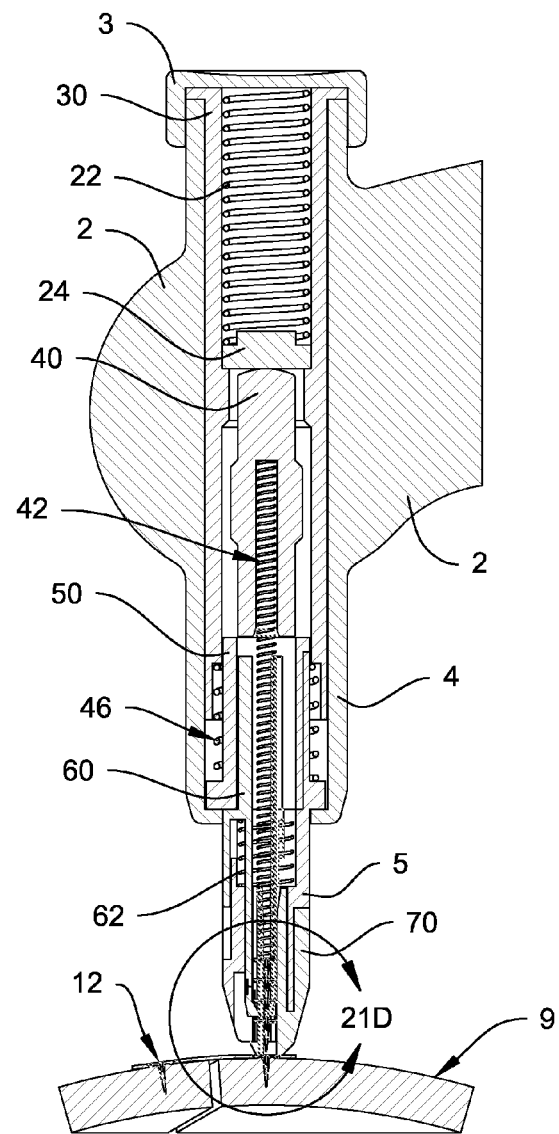
Figure 21C:
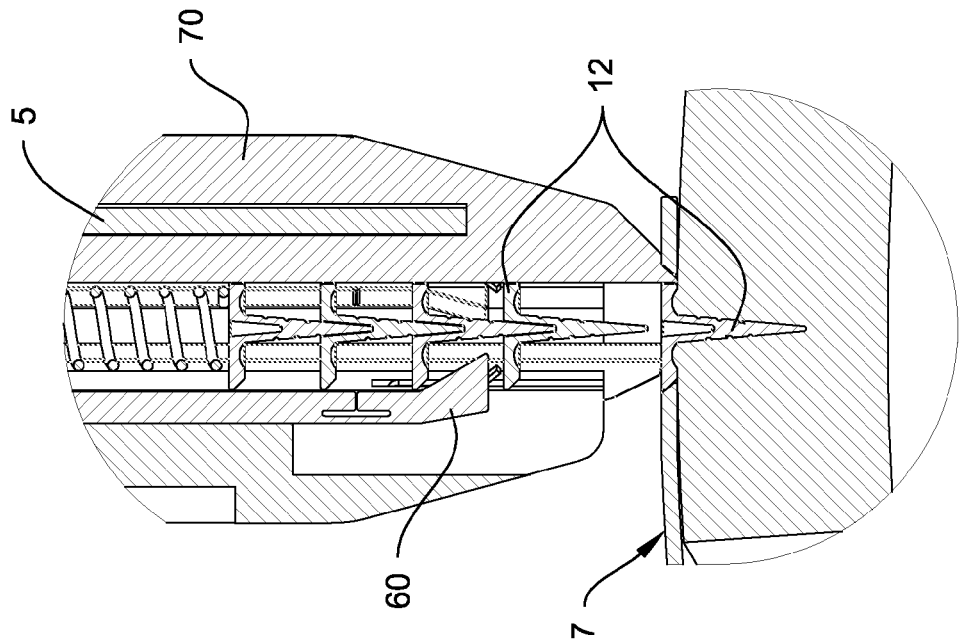
Figure 21D:
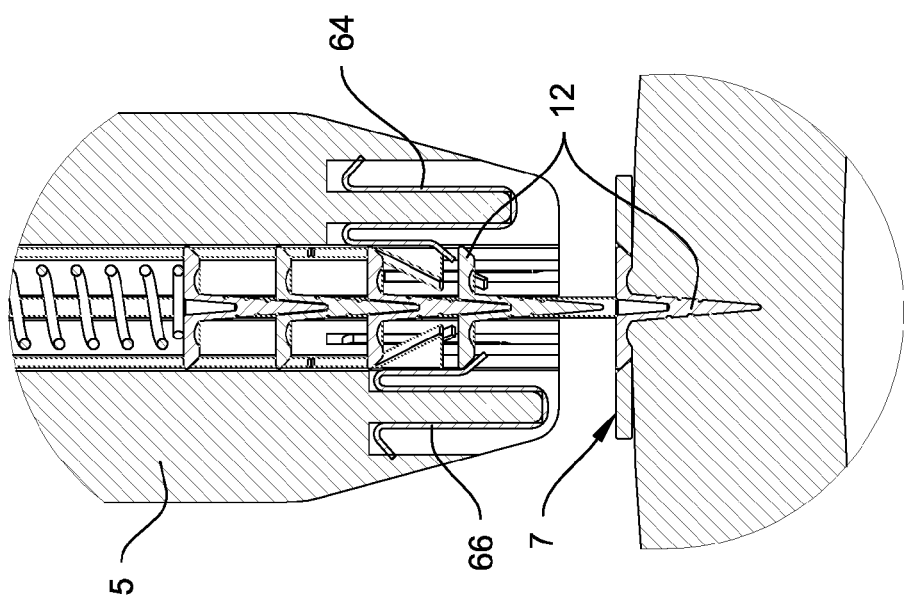
Figure 22A:
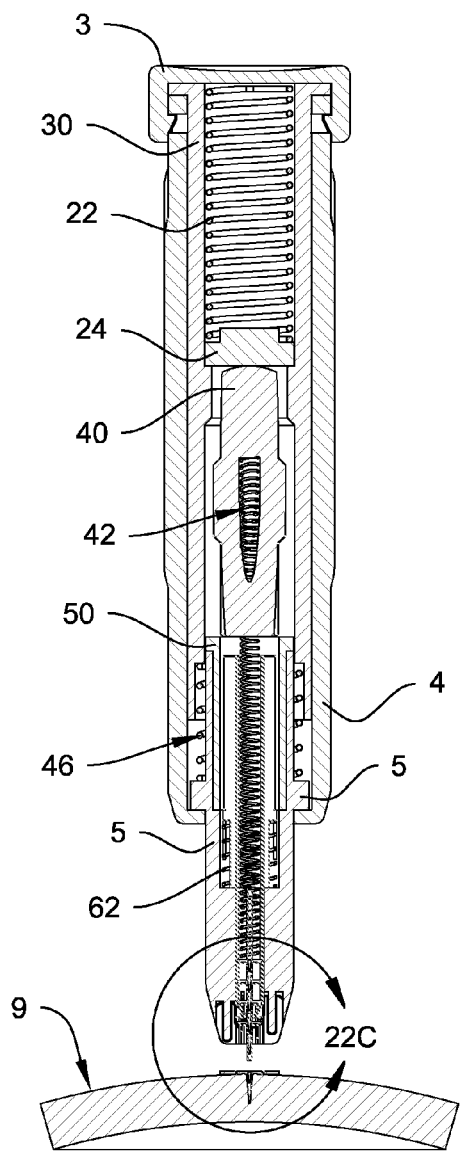
Figure 22B:
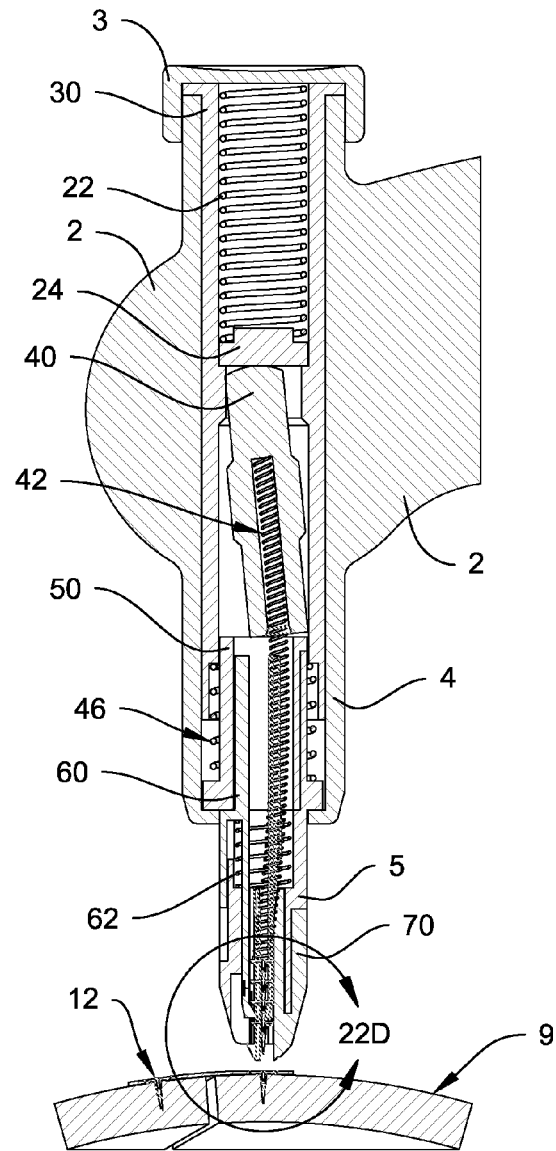
Figure 22D:
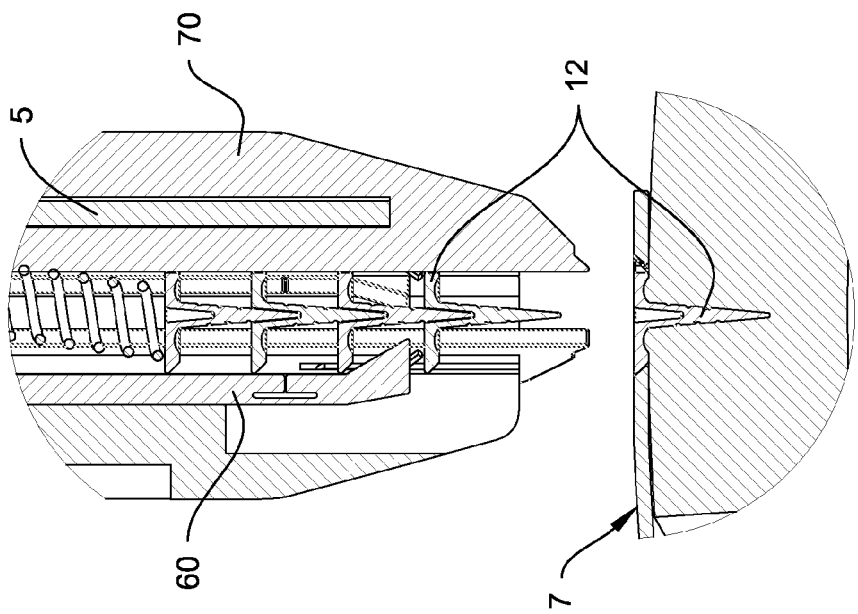
Figure 22C:
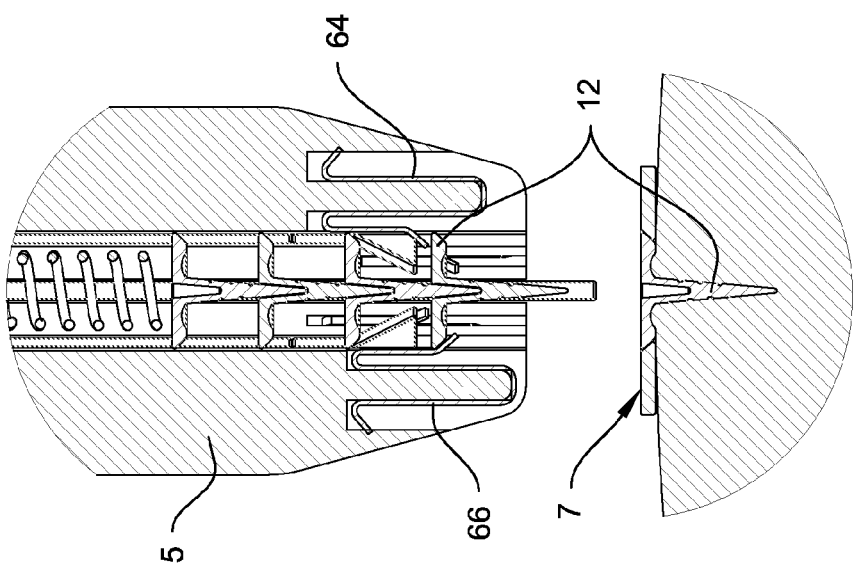

FIG. 15 is a top-down view of affixation tool 1.

FIGS. 16A-23D illustrate the operation of one embodiment of affixation tool 1. Each of the A views are taken along line A-A of FIG. 15. Each of the B views are taken along line B-B of FIG. 15.

Referring to FIGS. 16A-16D, affixation tool 1 is shown approaching, but not yet contacting, plate 20. In FIG. 14, hammer spring 22 is held in a compressed state between cap 3 and hammer plate 24. Hammer 40 is tilted with respect to a central axis of body tube 30. Because of its tilted position, hammer 40 is prevented from moving forward of hammer ring 504 of hammer sleeve 50.

Referring to FIGS. 17A-17D, alignment rails 80 contact pre-defined plate hole 152 in plate 30. In the illustrated embodiment, three alignment rails 80 contact plate hole 152, thereby centering the affixation tool 1. Other numbers of alignment rails or other methods of alignment can be used instead.

Referring to FIGS. 18A-18D, once affixation tool is aligned, a user (not shown) begins to press downwardly on handle 2, causing downward movement of body cylinder 4 and body sleeve 30 with respect to hammer 40. This downward movement further compresses hammer spring 22 and causes hammer orientation ring 312 to begin contacting hammer 40.

|Referring to FIGS. 19A-19D, continued downward movement of body sleeve 40 urges hammer orientation ring 312 against second segment 420 of hammer 40, causing hammer 40 to come into alignment with hammer sleeve 50.

Referring to FIGS. 20A-20D, once hammer 40 is sufficiently aligned with hammer sleeve 50, the force of hammer spring 22 causes hammer 40 to move quickly through hammer ring 512 into hammer sleeve 50. Hammer 40 then impacts hammer fingers 60, advancing hammer fingers 60 against the head portion 120 of leading fastener 12 and forcing fastener 12 past lower sequencing springs 66 and into bone 20. The following fastener 12 will be advanced past the upper sequencing spring(s) 64 by the compressed force of counterspring 42 and will be stopped by lower sequencing spring(s) 66.

Referring to FIGS. 21A-21D, as the user releases pressure and handle 2 returns to its original position, hammer tip 620 flexes outwardly at tip spring 630 around head portion 120 of the following fastener 12. The next fastener 12 is restrained by upper sequencing spring 64.

Referring to FIGS. 22A-22D, hammer 40 returns to its original canted position aided by the buckling action of counterspring 42. Hammer finger 60 returns to its original position aided by finger reset spring 62. Body cylinder 4 returns to its original position aided by body reset spring 46.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

I claim:

1. An apparatus for affixing a fastener to body tissue comprising:
    a tool body with hammer channel defined therein a hammer, the hammer channel having upper and lower ends and a central axis;
    a hammer positioned within the hammer channel;
    a hammer motor configured to provide a force tending to move the hammer toward the lower end of the hammer channel;
    a hammer canter configured to bias hammer at an angle with respect to the central axis;
    a hammer opening configured to prevent the hammer from moving downward unless hammer is substantially aligned with the central axis;
    an alignment device, connected to the tool body and configured so that relative movement between the tool body and the hammer will cause alignment device to contact the hammer and force the hammer toward alignment with the central axis; and
    a fastener impact device configured so that movement of the hammer past the hammer opening will transfer energy from the hammer or hammer motor to a fastener.

2. The apparatus of claim 1 wherein the hammer motor is a spring.

3. The apparatus of claim 1 wherein the fastener impact device comprises an extension of the hammer.

4. The apparatus of claim 1 wherein the fastener impact device comprises a hammer finger positioned between the hammer and a fastener.

5. The apparatus of claim 1 wherein the hammer canter comprises a spring extending through at least a portion of the hammer from a position below the hammer.

6. The apparatus of claim 1 wherein the fastener impact device is a hammer finger positioned between the hammer and a fastener.

7. The apparatus of claim 6 wherein the hammer finger comprises:
    a fastener tip angled toward the central axis; and
    a one-way spring configured to allow fasteners to pass downwardly past the fastener tip but to remain ridged against fasteners applying upward force.

* * * * *